(12) United States Patent
Speake et al.

(10) Patent No.: US 10,744,136 B2
(45) Date of Patent: Aug. 18, 2020

(54) SULFONAMIDE DERIVATIVES AS JAK INHIBITORS

(71) Applicant: Avista Pharma Solutions, Inc., Durham, NC (US)

(72) Inventors: Jason D. Speake, Winston-Salem, NC (US); Bharathi Pandi, Cary, NC (US); Joe B. Perales, Durham, NC (US); Weiming Fan, Chapel Hill, NC (US)

(73) Assignee: Avista Pharma Solutions, Inc., Durham, NC (US)

( * ) Notice: Subject to any disclaimer, the term of this patent is extended or adjusted under 35 U.S.C. 154(b) by 0 days.

(21) Appl. No.: 16/673,014

(22) Filed: Nov. 4, 2019

(65) Prior Publication Data

US 2020/0138811 A1 May 7, 2020

Related U.S. Application Data

(60) Provisional application No. 62/755,679, filed on Nov. 5, 2018.

(51) Int. Cl.
*C07D 487/04* (2006.01)
*A61K 31/4985* (2006.01)

(52) U.S. Cl.
CPC ........ *A61K 31/4985* (2013.01); *C07D 487/04* (2013.01)

(58) Field of Classification Search
CPC .................................................. C07D 487/04
See application file for complete search history.

(56) References Cited

U.S. PATENT DOCUMENTS

| 9,549,929 B2 | 1/2017 | Brown et al. |
| 2005/0171128 A1 | 8/2005 | Blumenkopf |
| 2010/0113420 A1 | 5/2010 | Salas-Solana |
| 2016/0045508 A1 | 2/2016 | Vazquez et al. |

FOREIGN PATENT DOCUMENTS

| WO | 2010020905 A1 | 2/2010 | |
| WO | WO2010/020905 | * 2/2010 | ........... C07D 487/04 |

OTHER PUBLICATIONS

Kisseleva, T., et al., "Signaling through the JAK/STAT Pathway, Recent Advances and Future Challenges", Gene, (2002), vol. 285, pp. 1-24.
Yamaoka, K., et al., "The Janus Kinases (JAKS)", Genome Biology, (2004), vol. 5, Issue 12, Article 253.
Cahn, R.S., et al., "Specification of Molecular Chirality", Angew. Chem. Internat. Edit, (1966), vol. 5, Mo. 4, pp. 385-415.
Errata, "Specification of Molecular Chirality", Angew. Chem., Int. Ed. (1966), vol. 5, p. 511.
Cruikshank, W.W., et al., "A Lipidated Anti-Tat Antibody Enters Living Cells and Blocks HIV-1 Viral Replication", Journal of Acquired Immune Deficiency Syndromes, (1997), vol. 14, No. 3, pp. 193-203.
Mata, P. and Lobo, A.M, "The CIP Sequence Rules: Analysis and Proposal for a Revision", Tetrahedron: Asymmetry (1993), vol. 4, No. 4, pp. 657-668.
Prelog, V. and Helmchen, G., "Basic Principles of the CIP-System and Proposals for a Revision", Angew. Chem. Int. Ed. Engl. (1982), vol. 21, pp. 567-583.
Zon, G., "Oligonucleoside Phosphorothioates", Methods in Molecular Biology, Protocols for Oligonucleotides and Analogs, vol. 20, Edited by Agrawal, S. (1993), pp. 165-189.
Ikebe, T., et al., "Successful Treatment of Refractory Enteropathy-Associated T-Cell Lymphoma Using High-Dose Chemotherapy and Autologous Stem Cell Transplantation", Internal Medicine (2010), vol. 49, pp. 2157-2161.
Vazquez, M.L., et al. "Identification of N-[cis-3-[Methyl(7H-pyrrolo[2,3-d]pyrimidin-4-yl)amino]cyclobutyl]propane-1-sulfonamide (PF-04965842): A Selective JAK1 Clinical Candidate for the Treatment of Autoimmune Diseases", J. Med. Chem., (2018), vol. 61, pp. 1130-1152.
International Search Report for PCT/US2019/059634, dated Apr. 10, 2020.

* cited by examiner

*Primary Examiner* — Paul V Ward
(74) *Attorney, Agent, or Firm* — Barnes & Thornburg LLP

(57) ABSTRACT

The present invention describes novel compounds, or their pharmaceutically acceptable salts, pharmaceutical compositions containing them, and their medical uses. The compounds of the invention have activity as Janus Kinase inhibitors and are useful in the treatment or control of pruritus, associated with allergic dermatitis, atopic dermatitis in animals, and other disorders and indications where immunosuppression/immunomodulation would be desirable. Also described herein are methods of treating pruritus and atopic dermatitis by administering the compounds of the invention, which are JAK 1 inhibitors.

6 Claims, No Drawings

SULFONAMIDE DERIVATIVES AS JAK INHIBITORS

CROSS-REFERENCE TO RELATED APPLICATIONS

This application claims the benefit of U.S. Provisional Patent Application No. 62/755,679, filed Nov. 5, 2018, the entire contents of which are hereby incorporated herein by reference.

FIELD OF THE INVENTION

The present invention describes novel compounds, or their pharmaceutically acceptable salts, pharmaceutical compositions containing them, and their medical uses. The compounds of the invention have activity as Janus Kinase (JAK) inhibitors and are useful in the in the treatment or control of pruritus, associated with allergic dermatitis, or atopic dermatitis in animals, and other disorders and indications where immunosuppression/immunomodulation would be desirable. Also described herein are methods of treating pruritus and atopic dermatitis by administering the compounds of the invention, which are JAK inhibitors.

BACKGROUND

Pruritus is defined as an unpleasant sensation that triggers an itch, namely a desire to scratch. Itch, like pain, is one of the body's basic defense mechanisms. A fundamental biologic function of itch is to alert an animal to the presence of potentially harmful toxins or other hazards such as disease-carrying insects, and to stimulate a reflex aimed at getting rid of these hazards. Itch can manifest acutely, like the reflex to remove fleas and other parasites. Alternatively, chronic itch, like pain, can be become self-perpetuating and pathologic in itself. Chronic itch results when peripheral and central nerves are over-stimulated, which leads to activation and proliferation of pruritus-mediating nerve fibers. Sensitized nerve fibers have been shown to more readily stimulate pruritus. Chronic itch necessitates more than symptomatic treatment, requiring a thorough diagnostic work-up to identify the underlying cause, and multimodal therapy to manage the insidious effects.

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dysregulation, or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases. Thus, protein kinases have emerged as an important class of enzymes as targets for therapeutic intervention. In particular, the JAK family of cellular protein tyrosine kinases (JAK-1, JAK-2, JAK-3, and Tyk-2) play a central role in cytokine signaling (Kisseleva et al, Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression, which stimulates biologic responses such as an itch signal. Activation of the JAK-STAT pathway also results in several other ancillary biologic activities that contribute to the inflammation and pruritic processes that contribute to acute allergy in animals but can also exacerbate clinical signs and contribute to chronic allergy.

There are substantial needs for safe and efficacious agents to control atopic dermatitis in animals, including mammals, birds, and fish. Examples of mammals include, but are not limited to, humans, cattle, sheep, goats, llamas, alpacas, pigs, horses, donkeys, dogs, cats, and other livestock or domestic mammals. Examples of birds include turkeys, chickens, ostriches, and other livestock or domestic birds. The market for treating atopic dermatitis in animals is currently dominated by corticosteroids, which cause distressing and undesirable side effects in animals, specifically in companion animals such as dogs. Antihistamines are also used, but are poorly effective. A formulation of cyclosporine (ATOPICA™) is currently being marketed for atopic dermatitis in dogs and cats, but is expensive and has a slow onset of efficacy. In addition, there are GI toleration issues with ATOPICA™. WO 2010/020905 discloses JAK inhibitors for the treatment of pruritus.

SUMMARY

Compounds of the present invention are novel JAK inhibitors with efficacy against JAK, including JAK 1. These compounds will be an alternative to steroid usage or JAK inhibitors already on the market and provide a resolution of chronic pruritus and inflammation that would either persist in atopic dermatitis or slowly regress following removal of allergen or causative agent, such as fleas in flea-allergic dermatitis.

One embodiment of the present invention includes a compound of Formula I or a pharmaceutical or veterinary salt thereof:

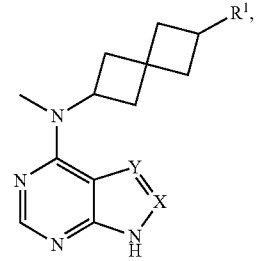

Formula I wherein
X is N, CH, or $CR^3$;
Y is N, CH, or $CR^3$;
$R^1$ is $(CH_2)_nSO_2N(R^2)_2$, $(CH_2)_mNHSO_2R^2$, $(CH_2)_nCON(R^2)_2$, or $(CH_2)_mNHCOR^2$
n is 0, 1, 2, 3, or 4;
m is 0, 1, 2, 3, or 4;
each $R^2$ individually is hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, unsubstituted or substituted cycloalkyl, unsubstituted or substituted aryl, or unsubstituted or substituted heteroaryl; or two R² may combine with the nitrogen to which they are attached to form an unsubstituted or substituted 5- to 7-membered ring, which may include one or more additional heteroatom selected from N, O, or S, and which may include one or more degrees of unsaturation;

and each R³ individually is $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, hydroxyl, $C_{1-6}$ alkoxy, $C_{1-6}$ haloalkyoxy, $C_{1-6}$ alkylsulfonyl, $C_{1-6}$ thioalkyl, mercapto, halogen, nitro, cyano, amino, $C_{1-6}$ alkylamino, unsubstituted or substituted cycloalkyl, unsubstituted or substituted aryl, or unsubstituted or substituted heteroaryl, when X is CR³ and Y is CR³, each CR³ may combine, with the atoms to which they are attached, to form a fused 5 to 7 membered ring.

In one embodiment, X is CH. In one embodiment, Y is CH. In one embodiment, both X and Y are CH.

In one embodiment, one or more of X and Y is CR³, where each R³ is halogen, cyano, or $C_{1-6}$ alkyl.

In one embodiment, R¹ is $(CH_2)_n SO_2 NHR^2$ or $(CH_2)_m NHSO_2 R^2$.

In one embodiment, n is 0 or 1. In one embodiment, m is 0 or 1.

In one embodiment, R² is $C_{1-6}$ alkyl, $C_{1-6}$ haloalkyl, unsubstituted or substituted cycloalkyl, or unsubstituted or substituted aryl. In one embodiment, R² is $C_{1-6}$ alkyl, $C_{1-6}$ haloalkyl, or unsubstituted or substituted cycloalkyl.

In one embodiment, the invention includes the compounds of formula (I) wherein R¹ is $(CH_2)_n SO_2 NHR^2$. In one embodiment, the invention includes the compounds of formula (I) wherein n is 0. In one embodiment, the invention includes the compounds of formula (I) wherein n is 1. In one embodiment, the invention includes the compounds of formula (I) wherein R² is $C_{1-6}$ alkyl. In one embodiment, the invention includes the compounds of formula (I) wherein R² is unsubstituted or substituted cycloalkyl. In one embodiment, the invention includes the compounds of formula (I) wherein R² is $C_{1-6}$ haloalkyl. In one embodiment, the invention includes the compounds of formula (I) wherein R² is unsubstituted or substituted aryl. In one embodiment, the invention includes the compounds of formula (I) wherein R² is aryl substituted with one or more halogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, CN, NO₂, NH₂, N($C_{1-6}$ alkyl)₂, OH, or $OC_{1-6}$ alkyl.

In one embodiment, the invention includes the compounds of formula (I) wherein R¹ is $(CH_2)_m NHSO_2 R^2$. In one embodiment, the invention includes the compounds of formula (I) wherein m is 0. In one embodiment, the invention includes the compounds of formula (I) wherein m is 1. In one embodiment, the invention includes the compounds of formula (I) wherein R² is $C_{1-6}$ alkyl. In one embodiment, the invention includes the compounds of formula (I) wherein R² is unsubstituted or substituted cycloalkyl. In one embodiment, the invention includes the compounds of formula (I) wherein R² is haloalkyl. In one embodiment, the invention includes the compounds of formula (I) wherein R² is unsubstituted or substituted aryl. In one embodiment, the invention includes the compounds of formula (I) wherein R² is aryl substituted with one or more halogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, CN, NO₂, NH₂, N($C_{1-6}$ alkyl)₂, OH, or $OC_{1-6}$ alkyl.

One embodiment includes a compound selected from:
N-methyl-6-[methyl(7H-pyrrolo[2,3-d]pyrimidin-4-yl)amino]spiro[3.3]heptane-2-sulfonamide;
N-ethyl-6-[methyl(7H-pyrrolo[2,3-d]pyrimidin-4-yl)amino]spiro[3.3]heptane-2-sulfonamide;
6-[methyl(7H-pyrrolo[2,3-d]pyrimidin-4-yl)amino]-N-propyl-spiro[3.3]heptane-2-sulfonamide;
N-isopropyl-6-[methyl(7H-pyrrolo[2,3-d]pyrimidin-4-yl)amino]spiro[3.3]heptane-2-sulfonamide;
N-cyclopropyl-6-[methyl(7H-pyrrolo[2,3-d]pyrimidin-4-yl)amino]spiro[3.3]heptane-2-sulfonamide;
6-[methyl(7H-pyrrolo[2,3-d]pyrimidin-4-yl)amino]-N-(2,2,2-trifluoroethyl)spiro[3.3]heptane-2-sulfonamide;
N-isobutyl-6-[methyl(7H-pyrrolo[2,3-d]pyrimidin-4-yl)amino]spiro[3.3]heptane-2-sulfonamide;
N-tert-butyl-6-[methyl(7H-pyrrolo[2,3-d]pyrimidin-4-yl)amino]spiro[3.3]heptane-2-sulfonamide;
N-cyclobutyl-6-[methyl(7H-pyrrolo[2,3-d]pyrimidin-4-yl)amino]spiro[3.3]heptane-2-sulfonamide;
N-cyclopentyl-6-[methyl(7H-pyrrolo[2,3-d]pyrimidin-4-yl)amino]spiro[3.3]heptane-2-sulfonamide;
N-[2-[methyl(7H-pyrrolo[2,3-d]pyrimidin-4-yl)amino]spiro[3.3]heptan-6-yl]benzenesulfonamide;
2-chloro-N-[2-[methyl(7H-pyrrolo[2,3-d]pyrimidin-4-yl)amino]spiro[3.3]heptan-6-yl]benzenesulfonamide;
4-chloro-N-[2-[methyl(7H-pyrrolo[2,3-d]pyrimidin-4-yl)amino]spiro[3.3]heptan-6-yl]benzenesulfonamide;
N-[2-[methyl(7H-pyrrolo[2,3-d]pyrimidin-4-yl)amino]spiro[3.3]heptan-6-yl]-4-(trifluoromethyl)benzenesulfonamide;
N-[2-[methyl(7H-pyrrolo[2,3-d]pyrimidin-4-yl)amino]spiro[3.3]heptan-6-yl]methanesulfonamide;
N-[2-[methyl(7H-pyrrolo[2,3-d]pyrimidin-4-yl)amino]spiro[3.3]heptan-6-yl]ethanesulfonamide;
N-[2-[methyl(7H-pyrrolo[2,3-d]pyrimidin-4-yl)amino]spiro[3.3]heptan-6-yl]propane-1-sulfonamide;
N-[2-[methyl(7H-pyrrolo[2,3-d]pyrimidin-4-yl)amino]spiro[3.3]heptan-6-yl]propane-2-sulfonamide;
2-methyl-N-[2-[methyl(7H-pyrrolo[2,3-d]pyrimidin-4-yl)amino]spiro[3.3]heptan-6-yl]propane-1-sulfonamide;
N-[2-[methyl(7H-pyrrolo[2,3-d]pyrimidin-4-yl)amino]spiro[3.3]heptan-6-yl]cyclopentanesulfonamide;
3,3,3-trifluoro-N-[2-[methyl(7H-pyrrolo[2,3-d]pyrimidin-4-yl)amino]spiro[3.3]heptan-6-yl]propane-1-sulfonamide;
N-((6-(methyl(7H-pyrrolo[2,3-d]pyrimidin-4-yl)amino)spiro[3.3]heptan-2-yl)methyl)methanesulfonamide;
N-((6-(methyl(7H-pyrrolo[2,3-d]pyrimidin-4-yl)amino)spiro[3.3]heptan-2-yl)methyl)ethanesulfonamide;
N-methyl-6-[methyl(9H-purin-6-yl)amino]spiro[3.3]heptane-2-sulfonamide;
(Enantiomer A)—N-methyl-6-[methyl(7H-pyrrolo[2,3-d]pyrimidin-4-yl)amino]spiro[3.3]heptane-2-sulfonamide;
(Enantiomer B)—N-methyl-6-[methyl(7H-pyrrolo[2,3-d]pyrimidin-4-yl)amino]spiro[3.3]heptane-2-sulfonamide;
6-[methyl(7H-pyrrolo[2,3-d]pyrimidin-4-yl)amino]spiro[3.3]heptane-2-sulfonamide;
N,N-dimethyl-6-[methyl(7H-pyrrolo[2,3-d]pyrimidin-4-yl)amino]spiro[3.3]heptane-2-sulfonamide;
N-methyl-N-(2-pyrrolidin-1-ylsulfonylspiro[3.3]heptan-6-yl)-7H-pyrrolo[2,3-d]pyrimidin-4-amine;
or a veterinary, or pharmaceutically acceptable salt thereof.

In one embodiment, the invention includes a composition comprising a compound of the present invention, and a pharmaceutically or veterinary acceptable carrier.

In one embodiment, the invention includes a combination comprising a compound of the present invention, and one or more other pharmaceutically or veterinary active substances.

In one embodiment, the invention includes a method for treating pruritus or atopic dermatitis comprising administering to a subject in need thereof an effective amount of a compound of the present invention. In one embodiment, the subject is an animal, including mammals, birds, and fish. Examples of mammals include, but are not limited to, humans, cattle, sheep, goats, llamas, alpacas, pigs, horses, donkeys, dogs, cats, and other livestock, domestic, or companion mammals. Examples of birds include turkeys, chickens, ostriches, and other livestock or domestic birds. In another embodiment, the subject is a mammal. In another embodiment, the subject is a companion animal.

In one embodiment, the invention includes a compound of the present invention for use in medicine.

In one embodiment, the invention includes a compound of the present invention for the manufacture of a medicament for the treatment of pruritus or atopic dermatitis.

In one embodiment, the invention includes use of a compound of the present invention for the treatment of pruritus or atopic dermatitis.

One or more aspects and embodiments may be incorporated in a different embodiment although not specifically described. That is, all aspects and embodiments can be combined in any way or combination.

DETAILED DESCRIPTION

Compounds of present invention are novel JAK inhibitors with efficacy against JAK, including JAK 1. These compounds will be an alternative to steroid usage and JAK inhibitors already on the market and provide a resolution of chronic pruritus and inflammation that would either persist in atopic dermatitis or slowly regress following removal of an allergen or causative agent, such as, for example, fleas in flea-allergic dermatitis.

Definitions

When referring to the compounds disclosed herein, the following terms have the following meanings unless indicated otherwise. The following definitions are meant to clarify, but not limit, the terms defined. If a particular term used herein is not specifically defined, such term should not be considered indefinite. Rather, terms are used within their accepted meanings.

As used herein, "alkyl" refers to monovalent saturated aliphatic hydrocarbyl groups having from 1 to 20 carbon atoms, preferably 1-8 carbon atoms, preferably 1-6 carbon atoms. The hydrocarbon chain can be either straight-chained or branched. Illustrative alkyl groups include methyl, ethyl, n-propyl, isopropyl, n-butyl, iso-butyl, and tert-butyl. Similarly, an "alkenyl" group refers to an alkyl group having one or more double bonds present in the chain, and an "alkynyl" group refers to an alkyl group having one or more triple bonds present in the chain.

As used herein, "aryl" refers to a carbocyclic aromatic ring system, either pendent or fused, such as phenyl, naphthyl, tetrahydronaphthyl, indane, or biphenyl.

As used herein, "cycloalkyl" refers to an unsaturated or partially saturated hydrocarbon ring, containing from 3 to 6 ring atoms. Illustrative cycloalkyl groups include cyclopropyl, cyclobutyl, cyclopentyl, cyclohexyl, as well as partially saturated versions thereof, such as cyclohexenyl, and cyclohexadienyl.

As used herein "halogen" or "halo" refers to a halogen. In some embodiments, the halogen is preferably Br, Cl, or F.

As used herein, "haloalkyl," "haloalkenyl," and "haloalkynyl" refers to each respective hydrocarbyl group having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms. The chain can be either straight-chained or branched. Illustrative haloalkyl groups include trifluoromethyl, trichloromethyl, trifluoroethyl, trifluoropropyl, trifluorobutyl, and pentafluoroethyl. Similarly, a "haloalkenyl" group refers to a haloalkyl group having one or more double bonds present in the chain, and a "haloalkenyl" group refers to a haloalkyl group having one or more triple bonds present in the chain.

The term "heteroaryl" or "heteroaromatic" refers to aromatic ring groups having five to fourteen ring atoms selected from carbon and at least one (typically 1-4, more typically 1 or 2) heteroatom (e.g., oxygen, nitrogen or sulfur). They include monocyclic rings and polycyclic rings in which a monocyclic heteroaromatic ring is fused to one or more other carbocyclic aromatic or heteroaromatic rings. Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl(e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl) and thienyl (e.g., 2-thienyl, 3-thienyl. Examples of monocyclic six-membered nitrogen-containing heteroaryl groups include pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl.

As used herein "optionally substituted" refers to a substitution of a hydrogen atom, which would otherwise be present on the substituent. When discussing ring systems, the optional substitution is typically with 1, 2, or 3 substituents replacing the normally-present hydrogen. When referencing straight and branched moieties, however, the number of substitutions can be more, occurring wherever hydrogen is usually present. The substitutions can be the same or different. Illustrative substitutions include nitro, —NR'R", cyano, —NR'COR'", alkyl, alkenyl, —C(O), —SO$_2$R'", —NR'SO$_2$R", —SO$_2$NR'R", —CONR'R", —CONHC$_6$H$_5$, hydroxy, alkoxy, alkylsulfonyl, haloalkyl, haloalkenyl, haloalkoxy, mercapto (—SH), thioalkyl, halogen, cycloalkyl, heterocyclyl, aryl, or heteroaryl, as each is understood in the art, and where R' and R" are the same or different and each represents hydrogen or alkyl; or when R' and R" are each attached to a nitrogen atom, they may form a saturated or unsaturated heterocyclic ring containing from 4 to 6 ring atoms, and wherein R'" is alkyl or haloalkyl.

As used herein the phrase veterinary or veterinarily, or pharmaceutical or pharmaceutically acceptable salt refers to any salt of a compound disclosed herein which retains its biological properties and which is not toxic or otherwise undesirable for veterinary or pharmaceutical use. Such salts may be derived from a variety of organic and inorganic counter-ions known in the art. Such salts include acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

Examples of inorganic bases that can be used to form base addition salts include, but are not limited to, metal hydroxides, such as lithium hydroxide, sodium hydroxide, and potassium hydroxide; metal amides, such as lithium amide and sodium amide; metal carbonates, such as lithium carbonate, sodium carbonate, and potassium carbonate; and ammonium bases such as ammonium hydroxide and ammonium carbonate.

Examples of organic bases that can be used to form base addition salts include, but are not limited to, metal alkoxides, such as lithium, sodium, and potassium alkoxides including lithium methoxide, sodium methoxide, potassium methoxide, lithium ethoxide, sodium ethoxide, potassium ethoxide, and potassium tert-butoxide; quaternary ammonium hydroxides, such as choline hydroxide; and amines including, but not limited to, aliphatic amines (i.e., alkylamines, alkenylamines, alkynylamines, and alicyclic amines), heterocyclic amines, arylamines, heteroarylamines, basic amino acids, amino sugars, and polyamines.

According to embodiments of the present invention, the base can be a quaternary ammonium hydroxide, wherein one or more of the alkyl groups of the quaternary ammonium ion are optionally substituted with one or more suitable substituents. Preferably, at least one alkyl group is substituted with one or more hydroxyl groups. Non-limiting examples of quaternary ammonium hydroxides that can be used in accordance with the present invention include choline hydroxide, trimethylethylammonium hydroxide, tetramethylammonium hydroxide, and is preferably choline hydroxide. According to embodiments of the present invention, an alkylamine base can be substituted or unsubstituted. Non-limiting examples of unsubstituted alkylamine bases that can be used in accordance with the present invention include methylamine, ethylamine, diethylamine, and triethylamine. A substituted alkylamine base is preferably substituted with one or more hydroxyl groups, and preferably one to three hydroxyl groups. Non-limiting examples of substituted alkylamine bases that can be used in accordance with the present invention include 2-(diethylamino)ethanol, N,N-dimethylethanolamine (deanol), tromethamine, ethanolamine, and diolamine.

In certain cases, the depicted substituents can contribute to optical and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78: 413-447, *Angew. Chem., Int. Ed. Engl.* 5: 385-414 (errata: *Angew. Chem., Int. Ed. Engl.* 5:511); Prelog and Helmchen, 1982, *Angew. Chem.* 94: 614-631, *Angew. Chem. Internat. Ed. Eng.* 21: 567-583; Mata and Lobo, 1993, *Tetrahedron: Asymmetry* 4: 657-668) or can be characterized by the manner in which the molecule rotates the plane of polarized light and is designated dextrorotatory or levorotatory (namely, as (+)- or (−)-isomers, respectively). A chiral compound can exist as either an individual enantiomer or as a mixture thereof. A mixture containing equal proportions of enantiomers is called a "racemic mixture".

In certain embodiments, the compounds disclosed herein can possess one or more asymmetric centers; and such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art.

In certain embodiments, the compounds disclosed herein are "stereochemically pure". A stereochemically pure compound has a level of stereochemical purity that would be recognized as "pure" by those of skill in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

As used herein, the terms "subject" and "patient" are used interchangeably herein. The terms "subject" and "subjects" refer to a human. In one embodiment, the subject is a companion animal such as a dog or cat. In a further embodiment the subject is an animal of agricultural importance such as a sheep, cow, horse, goat, fish, pig, or domestic fowl (such as a chicken, turkey, duck, or goose). In another embodiment the subject is a primate such as a monkey such as a cynomolgus monkey, a chimpanzee, and a human or non-primate animal.

In addition, a pharmaceutically acceptable prodrug of the compound represented by the formula (I) is also included in the present invention. The pharmaceutically acceptable prodrug refers to a compound having a group which can be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. The term prodrug is used throughout the specification to describe any pharmaceutically acceptable form of a compound which, upon administration to a patient, provides the active compound. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The present invention includes all pharmaceutically acceptable isotopically-labelled compounds of the invention wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labelled compounds of the invention, such as those incorporating a radioactive isotope, may be useful in drug or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described in the accompanying Examples and Preparations using an appropriate isotopically-labeled reagent in place of the non-labeled reagent previously employed.

Compositions and Methods of Administration

The compounds of formula (I) used in the methods disclosed herein can be administered in certain embodiments using veterinary or pharmaceutical compositions including at least one compound of formula (I), if appropriate in the salt form, either used alone or in the form of a combination with one or more compatible and veterinary or pharmaceutically acceptable carriers, such as diluents or adjuvants, or with another agent. There are provided compositions which comprise a derivative of formula (I) or a salt thereof, and an acceptable excipient, carrier or diluent. The composition can also be in a variety of forms which include, but are not limited to, oral formulations, injectable formulations, and topical, dermal or subdermal formulations.

The composition can be in a form suitable for oral use, for example, as dietary supplements, troches, lozenges, chewables, tablets, hard or soft capsules, emulsions, aqueous or oily suspensions, aqueous or oily solutions, dispersible powders or granules, syrups, or elixirs. Compositions intended for oral use can be prepared according to any method known in the art for the manufacture of veterinary or pharmaceutical compositions and such compositions can contain one or more agents selected from the group consisting of sweetening agents, bittering agents, flavoring agents, coloring agents and preserving agents in order to provide elegant and palatable preparations.

Lozenges are solid compositions containing one or more active ingredients intended to dissolve or disintegrate slowly in the oral cavity by passive incubation in the oral cavity, or actively by sucking or chewing. They can be used for systemic effect if the drug is absorbed through the buccal or esophageal lining or is swallowed. In particular, soft lozenges can be chewed or allowed to dissolve slowly in the mouth. These dosage forms have the advantage of being flavored and thus easy to administer to both human and animal patients; have formulas that are easy to change and can be patient specific; can deliver accurate amounts of the active ingredient to the oral cavity and digestive system; and allow for the drug to remain in contact with the oral or esophageal cavity for an extended period of time.

Tablets can contain the active ingredient in admixture with non-toxic, pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use can be hard gelatin capsules, wherein the active ingredient is mixed with an inert solid diluent, for example, calcium carbonate, calcium phosphate or kaolin. Capsules can also be soft gelatin capsules, wherein the active ingredient is mixed with water or miscible solvents such as propylene glycol, PEGs and ethanol, or an oil medium, for example, peanut oil, liquid paraffin, or olive oil.

The compositions can also be in the form of oil-in-water or water-in-oil emulsions. The oily phase can be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions can also contain sweetening agents, bittering agents, flavoring agents, and preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously. In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion. The aqueous phase includes, for example, water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol. Some compounds are common to the three components discussed above, for example, aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2.

In another embodiment for the amount of cosurfactant, there will be from about 25 to about 75% v/v of surfactant and from about 10 to about 55% v/v of cosurfactant in the microemulsion.

Oily suspensions can be formulated by suspending the active ingredient in a vegetable oil, for example, atachis oil, olive oil, sesame oil or coconut oil, or in mineral oil such as liquid paraffin. The oily suspensions can contain a thickening agent, for example, beeswax, hard paraffin or cetyl alcohol. Sweetening agents such as sucrose, saccharin or aspartame, bittering agents, and flavoring agents can be added to provide a palatable oral preparation. These compositions can be preserved by the addition of an anti-oxidant such as ascorbic acid, or other known preservatives.

Aqueous suspensions can contain the active material in admixture with excipients suitable for the manufacture of aqueous suspensions. Such excipients are suspending agents, for example, sodium carboxymethylcellulose, methylcellulose, hydroxypropylmethylcellulose, sodium alginate, polvinylpyrrolidone, gum tragacanth and gum acacia; dispersing or wetting agents can be a naturally-occuring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions can also contain one or more preservatives, for example, ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, can also be present.

Syrups and elixirs can be formulated with sweetening agents, for example, glycerol, propylene glycol, sorbitol or sucrose. Such formulations may also contain a demulcent, a preservative, flavoring agent(s) and coloring agent(s).

The compositions can be in the form of a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example, as a solution in 1,3-butane diol. Among the acceptable vehicles and solvents that can be employed are water, Ringer's solution and isotonic sodium chloride solution. Cosolvents such as ethanol, propylene glycol or polyethylene glycols can also be used. Preservatives, such as phenol or benzyl alcohol, can be used.

In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

Topical, dermal and subdermal formulations can include emulsions, creams, ointments, gels or pastes.

Organic solvents that can be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, compositions of the present invention may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Dosage forms can contain from about 0.5 mg to about 5 g of an active agent.

In one embodiment of the invention, the active agent is present in the formulation at a concentration of about 0.05 to 10% weight/volume.

The compounds of formula (I) can be employed as such or in the form of their preparations or formulations as combinations.

The compounds of formula (I) according to the invention may be combined with one or more agents having the same sphere of activity, for example, to increase activity, or with substances having another sphere of activity, for example, to broaden the range of activity. The compounds of formula (I) have been found to possess activity as JAK inhibitors. Thus, the compounds of the present invention may also be combined with other agents that inhibit JAK activity. Such JAK inhibitors can include small molecules, nucleic acids, e.g., JAK antisense nucleic acids, amino acids, peptides, carbohydrates, and anti-JAK antibodies. Preferably, such agents are combined with a pharmaceutically acceptable delivery vehicle or carrier. Examples of JAK antibodies include, for example, polyclonal, monoclonal, humanized, anti-idiotypic, chimeric or single chain antibodies, Fab, F(ab')$_2$, and Fab expression library fragments, scFV molecules, and epitope-binding fragments thereof. An antisense oligonucleotide directed to the JAK gene or mRNA to inhibit its expression is made according to standard techniques (see, e.g., Agrawal et al., *Methods in Molecular Biology: Protocols for Oligonucleotides and Analogs*, Vol. 20, (1993)). For anti-JAK antibodies, the preferred dosage is generally 0.2 mg/kg to 20 mg/kg body weight. Generally, partially humanized antibodies and fully human antibodies have a longer half-life within the human body than other antibodies. Accordingly, lower dosages and less frequent administration are possible. Modifications such as lipidation can be used to stabilize antibodies and to enhance uptake and tissue penetration. A method for lipidation of antibodies is described in Cruikshank et al., *J. Acquired Immune Deficiency Syndromes Hum. Retrovirol.* 14: 193, (1997).

The compounds of formula (I) according to the invention may be combined with one or more agents that modulate a mammalian immune system or with antiinflammatory agents. These agents may include but are not limited to cyclosporin A, e.g. Sandimmune® or Neoral®, rapamycin, FK-506 (tacrolimus), leflunomide, deoxyspergualin, mycophenolate, e.g., Cellcept®, azathioprine, e.g. Imuran®, daclizumab, e.g. Zenapax®, OKT3, e.g. Orthocolone®, AtGam, aspirin, acetaminophen, ibuprofen, naproxen, piroxicam, and antiinflammatory steroids, e.g. prednisolone or dexamethasone. These agents may be administered as part of the same or separate dosage forms, via the same or different routes of administration, and on the same or different administration schedules according to standard pharmaceutical practice known to one skilled in the art.

The pharmaceutical preparation comprising the compounds of formula (I), for delivery to a human or other mammal, is preferably in unit dosage form, in which the preparation is subdivided into unit doses containing an appropriate quantity of the active component. The unit dosage form can be a packaged preparation containing discrete quantities of the preparation, such as packaged tablets, capsules, and powders in vials or ampoules. Also, the unit dosage form can be a capsule, tablet or lozenge itself, or it can be an appropriate number of any of these in packaged form.

The quantity of active component in a unit dose preparation can be varied or adjusted from about 0.1 mg to about 1000 mg, according to the particular application and the potency of the active component. The composition can, if desired, also contain other compatible therapeutic agents.

In therapeutic use for the treatment or alleviation of pruritus, associated with allergic dermatitis, and atopic dermatitis in a human or other mammal, the compounds utilized in the method of treatment are administered at an initial dosage of about 0.1 mg/kg to about 100 mg/kg per interval, about 0.1 mg/kg to about 50.0 mg/kg per interval, about 0.1 mg/kg to about 10.0 mg/kg per interval, about 0.1 mg/kg to about 5.0 mg/kg per interval, about 0.1 mg/kg to about 2.5 mg/kg per interval, about 0.1 mg/kg to about 2.0 mg/kg per interval, about 0.1 mg/kg to about 1.0 mg/kg per interval, about 0.4 mg/kg to about 1.0 mg/kg per interval, or about 0.4 mg/kg to about 0.6 mg/kg per interval. Preferred intervals may be daily, weekly, monthly, quarterly, semi-annually, or annually. The dosages can be varied depending on the requirements of the patient, for example, the size of the human or mammal being treated, the severity of the condition being treated, the route of administration, and the potency of the compound(s) being used. Determination of the proper dosage and route of administration for a particular situation is within the skill of the practitioner. Generally, the treatment will be initiated with smaller dosages, which are less than the optimum dose of the compound, which can be increased in small increments until the optimum effect under the particular circumstances of the condition is reached. For convenience, the total daily dosage can be divided and administered in portions during the day if desired.

In therapeutic use, the compounds of formula (I) are useful in manufacture of a medicament for a method of the treating lupus, multiple sclerosis, rheumatoid arthritis, psoriasis, Type I diabetes and complications from diabetes, cancer, asthma, atopic dermatitis, autoimmune thyroid disorders, ulcerative colitis, Crohn's disease, Alzheimer's disease, leukemia, osteoarthritis, control of pruritus, chronic respiratory disease and other indications where immunosuppression/immunomodulation would be desirable.

The compounds of formula (I) may, in particular, be used in the fields of veterinary medicine, livestock husbandry and in particular, warm-blooded vertebrates, including companion animals such as dogs and cats, horses, livestock, and fowl.

The compounds of the present invention, stereoisomers thereof, and veterinary or pharmaceutically acceptable salts thereof, and compositions comprising compounds of the present invention in conjunction with at least one other veterinary agent are of particular value in the control of pruritus and atopic dermatitis in companion animals, particularly dogs and cats, livestock and birds.

Any of the compounds of the present invention, or a suitable combination of a compound of the present invention and optionally, with at least one additional veterinary agent may be administered directly to the animal and/or indirectly by applying it to the local environment in which the animal dwells (such as bedding, enclosures, and the like). Direct administration includes contacting the skin, fur, or feathers of a subject animal with the compound(s), or by feeding or injecting the compounds into the animal.

The Formula (I) compound, stereoisomer thereof, and veterinary acceptable salt thereof, and combinations with at least one additional veterinary agent, as described herein, are believed to be of value for the treatment and control of the various symptoms associated with pruritus and atopic dermatitis.

The present invention also relates to a method of administering a compound of the present invention alone or in combination with at least one additional veterinary agent, and optionally a veterinary acceptable excipient, diluent, or carrier, to animals in good health comprising the application to said animal to reduce or eliminate the symptoms associated with pruritus and atopic dermatitis.

The present invention explicitly encompasses those compounds presented in Table 1. A composition comprising a therapeutically acceptable amount of any of these compounds is also within the scope of the invention. The composition can further comprise a veterinary acceptable excipient, diluent, carrier, or mixture thereof. Such a composition can be administered to an animal in need thereof to treat or control pruritus and atopic dermatitis. The composition can further comprise an additional veterinary agent, as described herein.

TABLE 1

| Example | Compound Name |
|---|---|
| 1 | N-methyl-6-[methyl(7H-pyrrolo[2,3-d]pyrimidin-4-yl)amino]spiro[3.3]heptane-2-sulfonamide |
| 2 | N-ethyl-6-[methyl(7H-pyrrolo[2,3-d]pyrimidin-4-yl)amino]spiro[3.3]heptane-2-sulfonamide |
| 3 | 6-[methyl(7H-pyrrolo[2,3-d]pyrimidin-4-yl)amino]-N-propyl-spiro[3.3]heptane-2-sulfonamide |
| 4 | N-isopropyl-6-[methyl(7H-pyrrolo[2,3-d]pyrimidin-4-yl)amino]spiro[3.3]heptane-2-sulfonamide |
| 5 | N-cyclopropyl-6-[methyl(7H-pyrrolo[2,3-d]pyrimidin-4-yl)amino]spiro[3.3]heptane-2-sulfonamide |
| 6 | 6-[methyl(7H-pyrrolo[2,3-d]pyrimidin-4-yl)amino]-N-(2,2,2-trifluoroethyl)spiro[3.3]heptane-2-sulfonamide |
| 7 | N-isobutyl-6-[methyl(7H-pyrrolo[2,3-d]pyrimidin-4-yl)amino]spiro[3.3]heptane-2-sulfonamide |
| 8 | N-tert-butyl-6-[methyl(7H-pyrrolo[2,3-d]pyrimidin-4-yl)amino]spiro[3.3]heptane-2-sulfonamide |
| 9 | N-cyclobutyl-6-[methyl(7H-pyrrolo[2,3-d]pyrimidin-4-yl)amino]spiro[3.3]heptane-2-sulfonamide |
| 10 | N-cyclopentyl-6-[methyl(7H-pyrrolo[2,3-d]pyrimidin-4-yl)amino]spiro[3.3]heptane-2-sulfonamide |
| 11 | N-[2-[methyl(7H-pyrrolo[2,3-d]pyrimidin-4-yl)amino]spiro[3.3]heptan-6-yl]benzenesulfonamide |
| 12 | 2-chloro-N-[2-[methyl(7H-pyrrolo[2,3-d]pyrimidin-4-yl)amino]spiro[3.3]heptan-6-yl]benzenesulfonamide |
| 13 | 4-chloro-N-[2-[methyl(7H-pyrrolo[2,3-d]pyrimidin-4-yl)amino]spiro[3.3]heptan-6-yl]benzenesulfonamide |
| 14 | N-[2-[methyl(7H-pyrrolo[2,3-d]pyrimidin-4-yl)amino]spiro[3.3]heptan-6-yl]-4-(trifluoromethyl)benzenesulfonamide |
| 15 | N-[2-[methyl(7H-pyrrolo[2,3-d]pyrimidin-4-yl)amino]spiro[3.3]heptan-6-yl]methanesulfonamide |
| 16 | N-[2-[methyl(7H-pyrrolo[2,3-d]pyrimidin-4-yl)amino]spiro[3.3]heptan-6-yl]ethanesulfonamide |
| 17 | N-[2-[methyl(7H-pyrrolo[2,3-d]pyrimidin-4-yl)amino]spiro[3.3]heptan-6-yl]propane-1-sulfonamide |
| 18 | N-[2-[methyl(7H-pyrrolo[2,3-d]pyrimidin-4-yl)amino]spiro[3.3]heptan-6-yl]propane-2-sulfonamide |
| 19 | 2-methyl-N-[2-[methyl(7H-pyrrolo[2,3-d]pyrimidin-4-yl)amino]spiro[3.3]heptan-6-yl]propane-1-sulfonamide |
| 20 | N-[2-[methyl(7H-pyrrolo[2,3-d]pyrimidin-4-yl)amino]spiro[3.3]heptan-6-yl]cyclopentanesulfonamide |
| 21 | 3,3,3-trifluoro-N-[2-[methyl(7H-pyrrolo[2,3-d]pyrimidin-4-yl)amino]spiro[3.3]heptan-6-yl]propane-1-sulfonamide |
| 22 | N-((6-(methyl(7H-pyrrolo[2,3-d]pyrimidin-4-yl)amino)spiro[3.3]heptan-2-yl)methyl)methanesulfonamide |
| 23 | N-((6-(methyl(7H-pyrrolo[2,3-d]pyrimidin-4-yl)amino)spiro[3.3]heptan-2-yl)methyl)ethanesulfonamide |
| 24 | N-methyl-6-[methyl(9H-purin-6-yl)amino]spiro[3.3]heptane-2-sulfonamide |
| 25 | N-methyl-6-[methyl(1H-pyrazolo[3,4-d]pyrimidin-4-yl)amino]spiro[3.3]heptane-2-sulfonamide |
| 26 | (Enantiomer A)-N-methyl-6-[methyl(7H-pyrrolo[2,3-d]pyrimidin-4-yl)amino]spiro[3.3]heptane-2-sulfonamide |
| 27 | (Enantiomer B)-N-methyl-6-[methyl(7H-pyrrolo[2,3-d]pyrimidin-4-yl)amino]spiro[3.3]heptane-2-sulfonamide |
| 28 | 6-[methyl(7H-pyrrolo[2,3-d]pyrimidin-4-yl)amino]spiro[3.3]heptane-2-sulfonamide |
| 29 | N,N-dimethyl-6-[methyl(7H-pyrrolo[2,3-d]pyrimidin-4-yl)amino]spiro[3.3]heptane-2-sulfonamide |
| 30 | N-methyl-N-(2-pyrrolidin-1-ylsulfonylspiro[3.3]heptan-6-yl)-7H-pyrrolo[2,3-d]pyrimidin-4-amine |

Experimental Procedures

EXAMPLES

The following Examples provide a more detailed description of the process conditions for preparing compounds of the present invention. It is to be understood, however, that the invention, as fully described herein and as recited in the claims, is not intended to be limited by the details of the following schemes or modes of preparation.

Synthesis

Generally, the compounds of the present invention may be prepared, isolated or obtained by any method apparent to those of skill in the art. Exemplary methods of preparation are illustrated by the following schemes.

Scheme 1 (Example 1 as Illustrative):

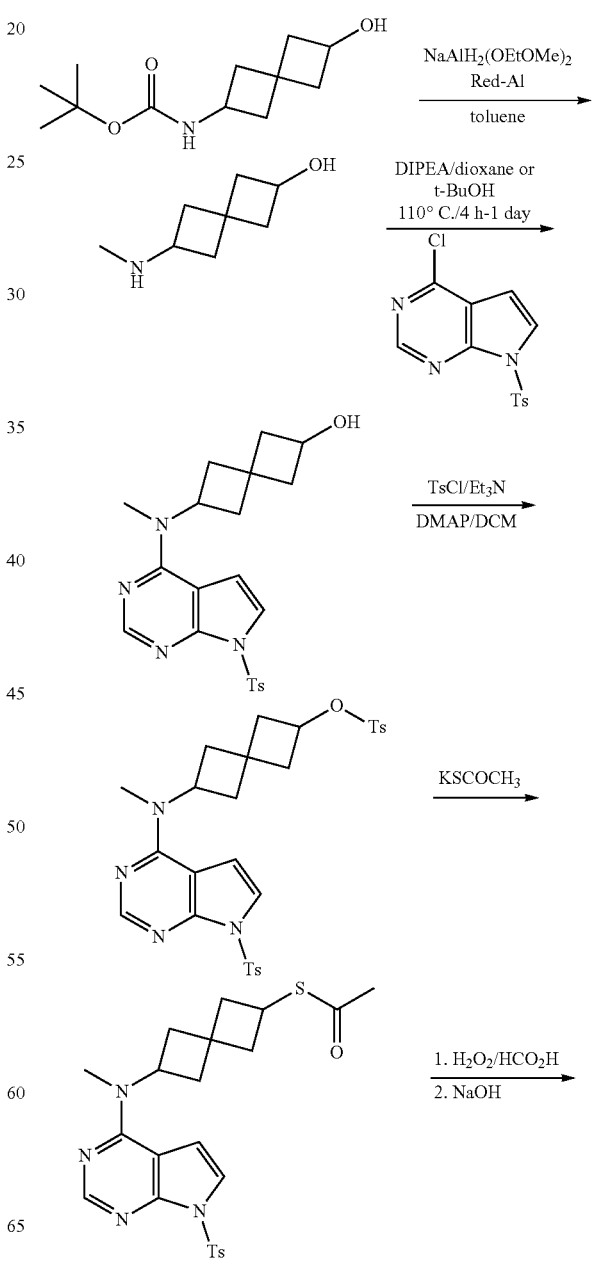

-continued

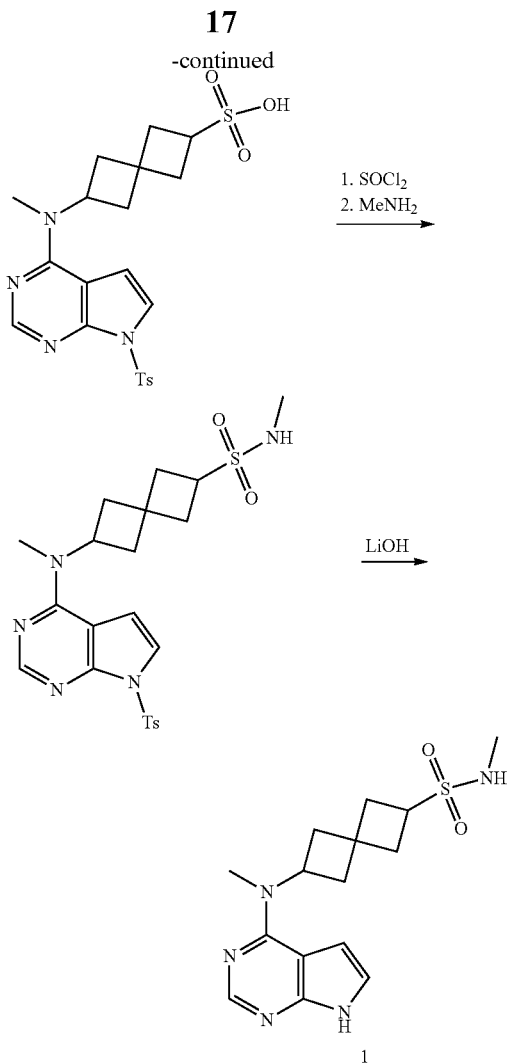

Example 1

Compound 1: N-methyl-6-[methyl(7H-pyrrolo[2,3-d]pyrimidin-4-yl)amino]spiro[3.3]heptane-2-sulfonamide

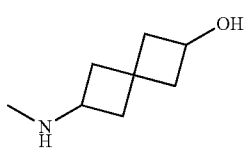

Intermediate 1: 6-(methylamino)spiro[3.3]heptan-2-ol

To a 1-liter flask was added tert-butyl N-(2-hydroxyspiro[3.3]heptan-6-yl)carbamate (16.0 g, 70 mmol) and toluene (200 mL). Red-Al (116 ml, 420 mmol, 70% in toluene) was added dropwise over 2 hours and internal temperature was controlled below 35° C. After addition, the mixture was slowly heated to 130° C. and stirred at that temperature for about 4 hours. Then it was cooled to <5° C. The mixture was quenched dropwise with saturated Na₂SO₄ solution (~200 mL). Internal temperature was controlled below 20° C. The solid was filtered and water solution was extracted with DCM (3×200 mL). The combined solution was dried over MgSO₄. After filtration and concentration in vacuo, it gave a viscous oil (9.0 g, 75%). ¹H NMR (400 MHz, METHANOL-d4) δ ppm 1.69-1.88 (m, 4H) 2.09-2.37 (m, 8H) 2.97-3.05 (m, 0.5 H) 3.23-3.32 (m, 8H) 3.36-3.40 (m, 1H) 3.42-3.48 (m, 1H) 3.57-3.62 (m, 4H) 3.99-4.07 (m, 0.5 H). LCMS (M/Z): 142 (M+H).

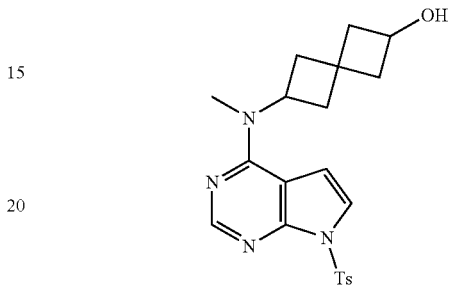

Intermediate 2: 6-[methyl-[7-(p-tolylsulfonyl)pyrrolo[2,3-d]pyrimidin-4-yl]amino]spiro[3.3]heptan-2-ol To a solution of 6-(methylamino)spiro[3.3]heptan-2-ol (8.46 g, ~60 mmol) in t-BuOH (140 mL) was added DIPEA (32 mL, 180 mmol) and 4-chloro-7-(p-tolylsulfonyl)pyrrolo[2,3-d]pyrimidine (18.4 g, 60 mmol). The mixture was heated at 110° C. for 1 day. The solvent was removed in vacuo. The residue was purified by an ISCO column (330 g eluting with EtOAc and heptane). After concentration, it gave an off white solid (17.0 g, 79.4%). ¹H NMR (400 MHz, DMSO-d6) δ ppm 1.82 (ddd, J=15.03, 10.93, 7.81 Hz, 2H) 2.06-2.24 (m, 5H) 2.29-2.40 (m, 4H) 3.10-3.14 (m, 3H) 3.18-3.27 (m, 1H) 3.90-3.99 (m, 1H) 4.88 (d, J=6.25 Hz, 1H) 4.97 (br t, J=8.59 Hz, 1H) 6.85 (d, J=4.10 Hz, 1H) 7.39 (m, J=8.00 Hz, 2H) 7.57 (d, J=4.10 Hz, 1H) 7.93 (m, J=8.20 Hz, 2H) 8.19 (s, 1H); LCMS (M/Z): 413 (M+H).

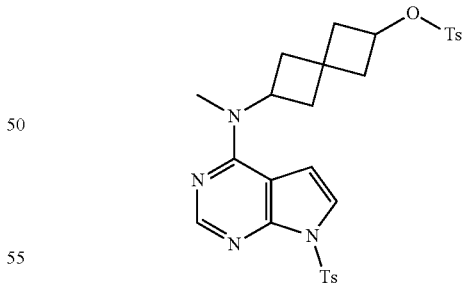

Intermediate 3: [6-[methyl-[7-(p-tolylsulfonyl)pyrrolo[2,3-d]pyrimidin-4-yl]amino]spiro[3.3]heptan-2-yl] 4-methylbenzenesulfonate To a 1 liter round bottom flask was added 6-[methyl-[7-(p-tolylsulfonyl)pyrrolo[2,3-d]pyrimidin-4-yl]amino]spiro[3.3]heptan-2-ol (~22.3 g, 54.1 mmol), DCM (200 mL), DMAP (1.31 g, 10.8 mmol), Et₃N (15.3 ml, 108.2 mmol), and TsCl (11.9 g, 62.2 mmol). The reaction was carried out at room temperature for about 20 hours, monitoring by LCMS. Then the mixture was treated with water (100 mL). The aqueous solution was extracted with DCM (100 mL×2). The combined organic solution was dried over Na$_2$SO$_4$. After filtration and concentration, it gave a light brown solid (38.3 g). The crude material was purified by ISCO (330 g column) and eluted with EtOAc and heptane. It gave a light yellow solid (29.4 g, 96%). $^1$H NMR (400 MHz, DMSO-d6) δ ppm) 1.20 (s, 1H) 1.99-2.25 (m, 7H) 2.32 (s, 4H) 2.40 (s, 4H) 3.09 (s, 3H) 4.69 (t, J=7.22 Hz, 1H) 4.92 (s, 1H) 5.72 (s, 1H) 6.84 (d, J=4.10 Hz, 1H) 7.36-7.47 (m, 5H) 7.56 (d, J=4.30 Hz, 1H) 7.75 (d, J=8.40 Hz, 2H) 7.92 (d, J=8.40 Hz, 2H) 8.17 (s, 1H); LCMS (M/Z): 567 (M+H).

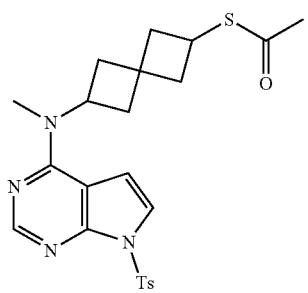 [SMILES: CC(=O)SC1CC2(C1)CC(N(C)c1ncnc3c1ccn3S(=O)(=O)c1ccc(C)cc1)C2]

Intermediate 4: S-[6-[methyl-[7-(p-tolylsulfonyl)pyrrolo[2,3-d]pyrimidin-4-yl]amino]spiro[3.3]heptan-2-yl] ethanethioate To a 1-liter round bottom flask containing the compound 6-[methyl-[7-(p-tolylsulfonyl)pyrrolo[2,3-d]pyrimidin-4-yl]amino]spiro[3.3]heptan-2-yl]4-methylbenzenesulfonate (29.4 g, ~51.9 mmol) was added DMSO (200 mL) and potassium thioacetate (~33.1 g, 289 mmol). The reaction was heated at 60° C. for 20 hours, monitoring by LCMS. Then, it was treated with 5% NaHCO$_3$ (200 mL) and extracted with EtOAc (3×200 mL). The combined organic solution was dried over Na$_2$SO$_4$. After filtration and concentration. It gave a light brownish solid (25.3 g, ~100%). LCMS (M/Z): 471 (M+H). It was used directly for next step without further purification.

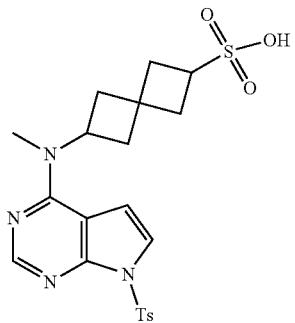 [SMILES: Cc1ccc(S(=O)(=O)n2ccc3c(N(C)C4CC5(C4)CC(S(=O)(=O)O)C5)ncnc32)cc1]

Intermediate 5: 6-[methyl-[7-(p-tolylsulfonyl)pyrrolo[2,3-d]pyrimidin-4-yl]amino]spiro[3.3]heptane-2-sulfonic acid To a 1 liter three-neck flask equipped with a thermometer, additional funnel, and nitrogen adapter was added S-[6-[methyl-[7-(p-tolylsulfonyl)pyrrolo[2,3-d]pyrimidin-4-yl]amino]spiro[3.3]heptan-2-yl] ethanethioate (~9.8 g, ~20 mmol) and formic acid (80 mL). Then H$_2$O$_2$ (30% in water, ~25 mL) was added over 1.5 hours. It was cooled by water bath with ice as needed to keep the temperature under 35° C. After the addition, the reaction mixture was cooled to room temperature and stirred at room temperature for 30 min. After cooling down to 0-5° C., the reaction mixture was quenched with NaHSO$_3$ and Na$_2$S$_2$O$_5$ (33% in water, ~100 mL) portion wise keeping the temperature under 35° C. An aqueous solution of NaOH (33%) was added at 0-5° C. until pH=4-5 was reached (internal temp was controlled <35° C.). The resulting white solid was filtered and dried over pump overnight. It gave a tan solid (~16.6 g, containing salts, 60% purity). $^1$H NMR (400 MHz, METHANOL-d4) δ ppm 2.21-2.39 (m, 4H) 2.40 (s, 3H) 2.42-2.50 (m, 3H) 2.51-2.57 (m, 1H) 3.22-3.24 (s, 3H) 3.51 (quin, J=8.36 Hz, 1H) 4.92-5.01 (m, 1H) 6.85 (d, J=4.15 Hz, 1H) 7.37 (d, J=8.54 Hz, 2H) 7.56 (d, J=4.15 Hz, 1H) 7.95-8.00 (m, 2H) 8.20 (s, 1H) 8.42 (s, 2H, HCO$_2$Na); LCMS (M/Z): 477 (M+H).

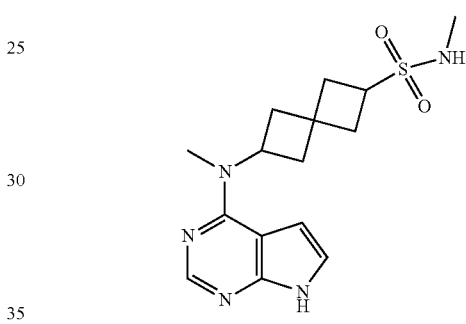

N-methyl-6-[methyl(7H-pyrrolo[2,3-d]pyrimidin-4-yl)amino]spiro[3.3]heptane-2-sulfonamide, Compound 1

Intermediate 5, 6-[methyl-[7-(p-tolylsulfonyl)pyrrolo[2,3-d]pyrimidin-4-yl]amino]spiro[3.3]heptane-2-sulfonic acid (~476 mg, crude, containing salts, ~0.66 mmol) was suspended in DCM (4 mL). Then SOCl$_2$ (4 mL) was added followed by 4 drops of DMF. The reaction mixture was then heated to reflux for 4 h (heating block temp at 55-60° C. Then the reaction mixture was cooled to room temperature. Dry toluene was added to the solution. The solvent was removed in vacuo. The residue was taken up in THF (2 mL) and excess CH$_3$NH$_2$ (2M in THF, 4 mL) was added. The reaction mixture was stirred overnight. Then the reaction mixture was treated with water (~10 mL) and extracted with EtOAc (3×20 mL). After the removal of solvent, the residue was further purified by C18 ISCO column (50 g) and eluted with MeOH and water. After the removal of solvent, it gave a white solid (~274 mg, ~85%). To a solution of the sulfonamide (274 mg, ~0.54 mmol) in isopropanol (4 mL) and water (3 mL) was added LiOH.H$_2$O (419 mg, 10 mmol). The mixture was stirred at 50-55° C. for 4 hours and room temperature for overnight. After the removal of the solvent, the residue was dissolved in water (~2 mL) and MeOH (~1 mL). It was purified by C18 ISCO column (50 g) and eluted with MeOH and water. After concentration, it gave the white solid (128 mg, 71%). $^1$H NMR (400 MHz, METHANOL-d4) δ ppm 2.27-2.42 (m, 4H) 2.42-2.61 (m, 4H) 2.68 (s, 3H) 3.27 (s, 3H) 3.86 (quin, J=8.25 Hz, 1H) 5.05 (quin, J=8.54

Hz, 1H) 6.61 (d, J=3.51 Hz, 1H) 7.07 (d, J=3.51 Hz, 1H) 8.07 (s, 1H); LCMS (M/Z): 336 (M+H).

By proceeding in a similar manner, the following compounds were also prepared.

Example 2

Compound 2: N-ethyl-6-[methyl(7H-pyrrolo[2,3-d]pyrimidin-4-yl)amino]spiro[3.3]heptane-2-sulfonamide

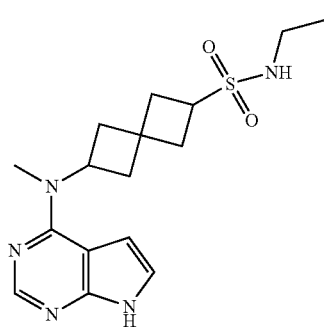

N-ethyl-6-[methyl(7H-pyrrolo[2,3-d]pyrimidin-4-yl)amino]spiro[3.3]heptane-2-sulfonamide 2: $^1$H NMR (400 MHz, METHANOL-d4) δ ppm 1.15 (t, J=7.22 Hz, 3H) 2.26-2.60 (m, 9H) 3.07 (q, J=7.22 Hz, 2H) 3.82 (quin, J=8.30 Hz, 1H) 4.99-5.13 (m, 1H) 6.61 (d, J=3.51 Hz, 1H) 7.08 (d, J=3.71 Hz, 1H) 8.07 (s, 1H); LCMS (M/Z): 350 (M+H).

Example 3

Compound 3: 6-[methyl(7H-pyrrolo[2,3-d]pyrimidin-4-yl)amino]-N-propyl-spiro[3.3]heptane-2-sulfonamide

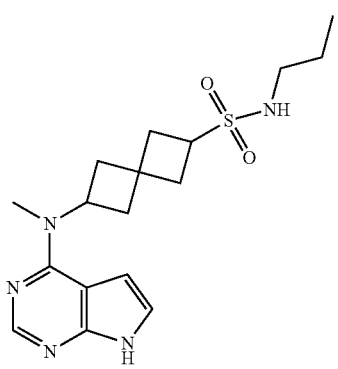

6-[methyl(7H-pyrrolo[2,3-d]pyrimidin-4-yl)amino]-N-propyl-spiro[3.3]heptane-2-sulfonamide 3: $^1$H NMR (400 MHz, METHANOL-d4) δ ppm 0.93 (t, J=7.32 Hz, 3H) 1.53 (sxt, J=7.26 Hz, 2H) 2.26-2.57 (m, 8H) 2.98 (t, J=7.13 Hz, 2H) 3.75-3.89 (m, 1H) 4.96-5.12 (m, 1H) 6.61 (d, J=3.71 Hz, 1H) 7.08 (d, J=3.71 Hz, 1H) 8.07 (s, 1H); LCMS (M/Z): 364 (M+H).

Example 4

Compound 4: N-isopropyl-6-[methyl(7H-pyrrolo[2,3-d]pyrimidin-4-yl)amino]spiro[3.3]heptane-2-sulfonamide

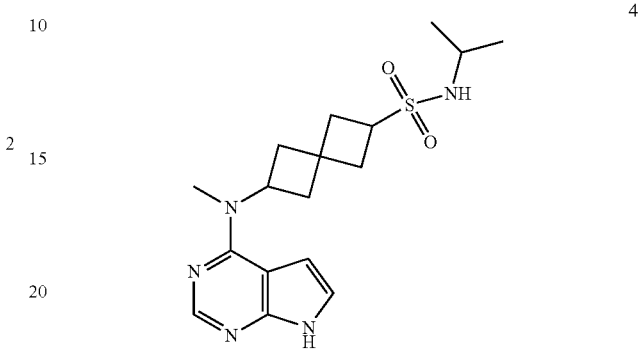

N-isopropyl-6-[methyl(7H-pyrrolo[2,3-d]pyrimidin-4-yl)amino]spiro[3.3]heptane-2-sulfonamide 4: $^1$H NMR (400 MHz, METHANOL-d4) δ ppm 1.17 (d, J=6.64 Hz, 6H) 2.23-2.60 (m, 8H) 3.51 (dt, J=13.18, 6.49 Hz, 1H) 3.72-3.87 (m, 1H) 5.00-5.13 (m, 1H) 6.61 (d, J=3.71 Hz, 1H) 7.08 (d, J=3.51 Hz, 1H) 8.07 (s, 1H); LCMS (M/Z): 364 (M+H).

Example 5

Compound 5: N-cyclopropyl-6-[methyl(7H-pyrrolo[2,3-d]pyrimidin-4-yl)amino]spiro[3.3]heptane-2-sulfonamide

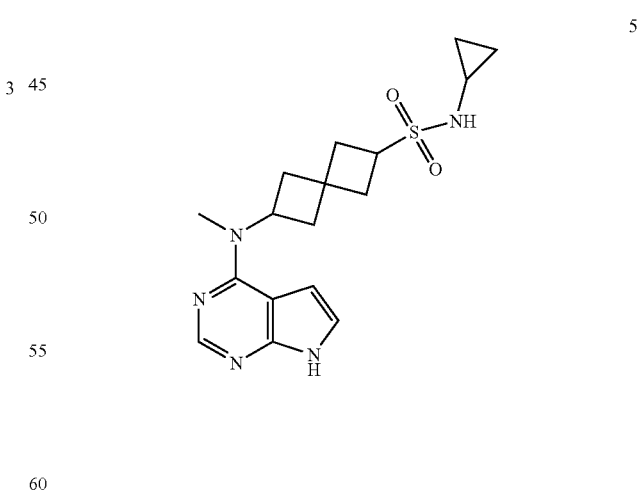

N-cyclopropyl-6-[methyl(7H-pyrrolo[2,3-d]pyrimidin-4-yl)amino]spiro[3.3]heptane-2-sulfonamide 5: $^1$H NMR (400 MHz, METHANOL-d4) δ ppm 0.52-0.72 (m, 4H) 2.25-2.65 (m, 10H) 3.93 (quin, J=8.30 Hz, 1H) 4.98-5.13 (m, 1H) 6.62 (d, J=3.71 Hz, 1H) 7.08 (d, J=3.51 Hz, 1H) 8.07 (s, 1H); LCMS (M/Z): 362 (M+H).

Example 6

Compound 6: 6-[methyl(7H-pyrrolo[2,3-d]pyrimidin-4-yl)amino]-N-(2,2,2-trifluoroethyl)spiro[3.3]heptane-2-sulfonamide

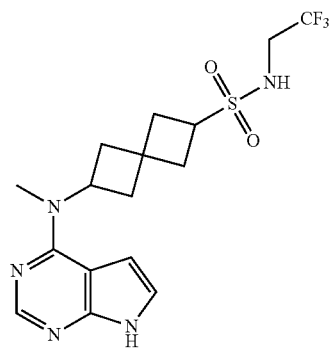

6-[methyl(7H-pyrrolo[2,3-d]pyrimidin-4-yl)amino]-N-(2,2,2-trifluoroethyl)spiro[3.3]heptane-2-sulfonamide 6: $^1$H NMR (400 MHz, METHANOL-d4) δ ppm 2.24-2.61 (m, 8H) 3.72 (q, J=9.18 Hz, 2H) 3.84 (quin, J=8.25 Hz, 1H) 4.98-5.13 (m, 1H) 6.61 (d, J=3.71 Hz, 1H) 7.08 (d, J=3.71 Hz, 1H) 8.07 (s, 1H); LCMS (M/Z): 404 (M+H).

Example 7

Compound 7: N-isobutyl-6-[methyl(7H-pyrrolo[2,3-d]pyrimidin-4-yl)amino]spiro[3.3]heptane-2-sulfonamide

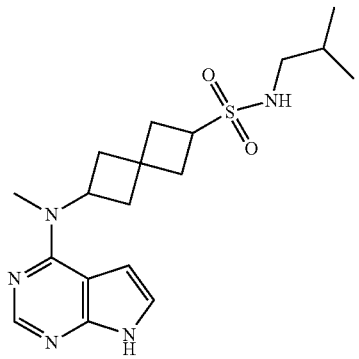

N-isobutyl-6-[methyl(7H-pyrrolo[2,3-d]pyrimidin-4-yl)amino]spiro[3.3]heptane-2-sulfonamide 7: $^1$H NMR (400 MHz, METHANOL-d4) δ ppm 0.92 (d, J=6.83 Hz, 6H) 1.71 (dt, J=13.47, 6.74 Hz, 1H) 2.28-2.57 (m, 8H) 2.83 (d, J=6.83 Hz, 2H) 3.81 (t, J=8.30 Hz, 1H) 4.98-5.15 (m, 1H) 6.61 (d, J=3.51 Hz, 1H) 7.08 (d, J=3.71 Hz, 1H) 8.07 (s, 1H); LCMS (M/Z): 378 (M+H).

Example 8

Compound 8: N-tert-butyl-6-[methyl(7H-pyrrolo[2,3-d]pyrimidin-4-yl)amino]spiro[3.3]heptane-2-sulfonamide

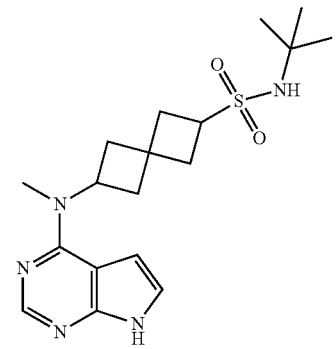

N-tert-butyl-6-[methyl(7H-pyrrolo[2,3-d]pyrimidin-4-yl)amino]spiro[3.3]heptane-2-sulfonamide 8: $^1$H NMR (400 MHz, METHANOL-d4) δ ppm 1.34 (s, 9H) 2.31-2.43 (m, 4H) 2.47-2.61 (m, 4H) 3.80 (quin, J=8.29 Hz, 1H) 5.04-5.13 (m, 1H) 6.65 (d, J=3.66 Hz, 1H) 7.11 (d, J=3.66 Hz, 1H) 8.11 (s, 1H); LCMS (M/Z): 378 (M+H).

Example 9

Compound 9: N-cyclobutyl-6-[methyl(7H-pyrrolo[2,3-d]pyrimidin-4-yl)amino]spiro[3.3]heptane-2-sulfonamide

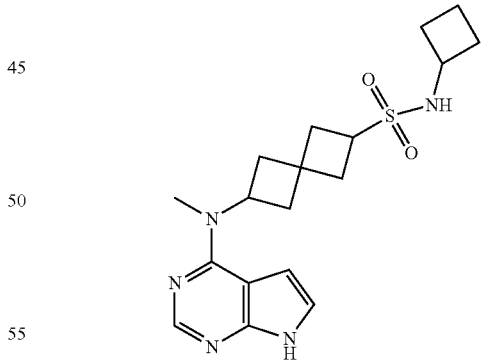

N-cyclobutyl-6-[methyl(7H-pyrrolo[2,3-d]pyrimidin-4-yl)amino]spiro[3.3]heptane-2-sulfonamide 9: $^1$H NMR (400 MHz, METHANOL-d4) δ ppm 1.53-1.72 (m, 2H) 1.99 (ddd, J=10.92, 9.21, 1.83 Hz, 2H) 2.28-2.47 (m, 8H) 2.48-2.56 (m, 3H) 2.86 (s, 1H) 3.30-3.31 (m, 3H) 3.73 (t, J=8.29 Hz, 1H) 3.84 (dd, J=8.78, 7.81 Hz, 1H) 4.91-5.12 (m, 1H) 6.65 (d, J=3.66 Hz, 1H) 7.11 (d, J=3.66 Hz, 1H) 8.11 (s, 1H); LCMS (M/Z): 376 (M+H).

Example 10

Compound 10: N-cyclopentyl-6-[methyl(7H-pyrrolo[2,3-d]pyrimidin-4-yl)amino]spiro[3.3]heptane-2-sulfonamide

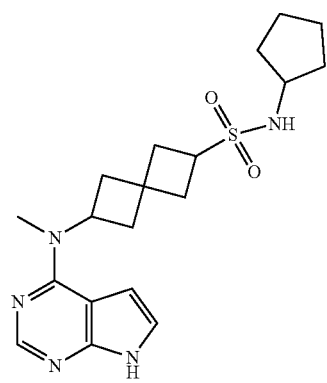

N-cyclopentyl-6-[methyl(7H-pyrrolo[2,3-d]pyrimidin-4-yl)amino]spiro[3.3]heptane-2-sulfonamide 10: $^1$H NMR (400 MHz, METHANOL-d4) δ ppm 1.46-1.64 (m, 5H) 1.68-1.77 (m, 2H) 1.90-2.00 (m, 2H) 2.33-2.44 (m, 4H) 2.47-2.61 (m, 4H) 3.66-3.73 (m, 1H) 3.84 (quin, J=8.29 Hz, 1H) 5.04-5.13 (m, 1H) 6.65 (d, J=3.66 Hz, 1H) 7.11 (d, J=3.66 Hz, 1H) 8.11 (s, 1H); LCMS (M/Z): 390 (M+H).

Example 11

Compound 11: N-[2-[methyl(7H-pyrrolo[2,3-d]pyrimidin-4-yl)amino]spiro[3.3]heptan-6-yl]benzenesulfonamide Scheme 2 (Example 11 as Illustrative):

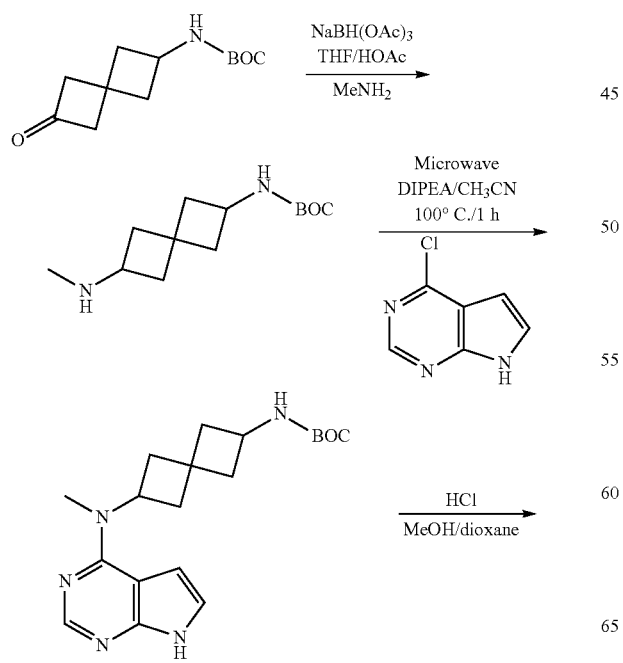

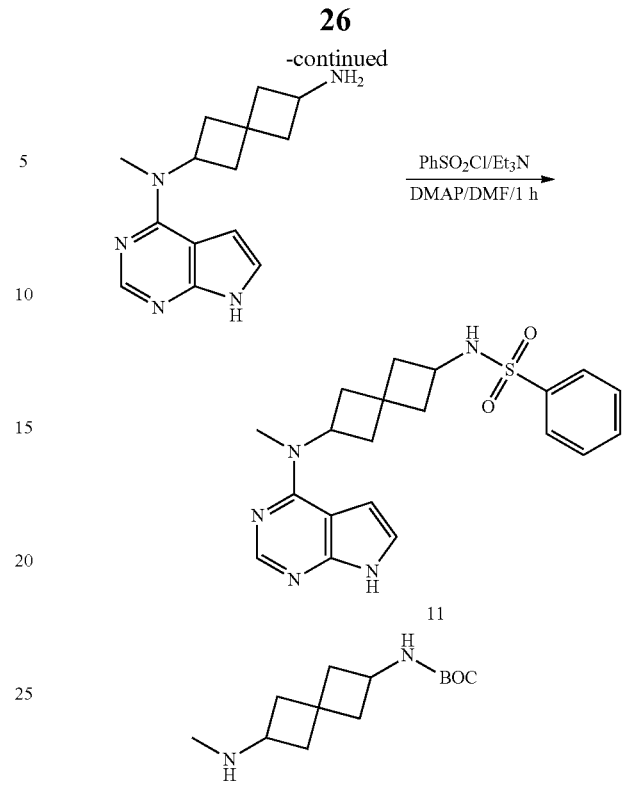

Intermediate 1: tert-butyl N-[6-(methylamino)spiro[3.3]heptan-2-yl]carbamate

To a solution of tert-butyl N-(2-oxospiro[3.3]heptan-6-yl)carbamate (2.08 g, 9.2 mmol) in THF (50 mL) was added MeNH$_2$ (13 mL, 26 mmol). The mixture was stirred at about −20° C. for 3 hours and then room temperature over weekend. After cooled to about-20° C. and stirred for 2 hours, NaBH(OAc)$_3$ (6.32 g, 30 mmol) was added. The mixture was stirred for 1 h and treated with 10% NaHCO$_3$ (30 mL). Then it was treated with 10% NaOH up to pH=~11. It was extracted with DCM (3×40 mL). The combined organic solution was dried over Na$_2$SO$_4$. After filtration and concentration, it gave the product as colorless oil (~2.40 g, 100%). LCMS (M/Z): 241 (M+H). The material was used directly for the next step without purification.

Intermediate 2: tert-butyl N-[2-[methyl(7H-pyrrolo[2,3-d]pyrimidin-4-yl)amino]spiro[3.3]heptan-6-yl]carbamate To a microwave vial were added tert-butyl N-[6-(methylamino)spiro[3.3]heptan-2-yl]carbamate (0.96 g, 4.0 mmol, crude), 4-chloro-7H-pyrrolo[2,3-d]pyrimidine (0.61 g, 4.0 mmol), DIPEA (1.03 mL, 8.0 mmol), and CH$_3$CN (6 mL). The mixture was heated at 100° C. for 1 h in microwave (75 W and 250 psi). The reaction was cooled to room temperature and allowed to stand. The solid (product) was filtered and washed with CH$_3$CN. The filtrate was concentrated and dried over vacuum. The combined solids were an off white solid (~0.66 g, 46%). $^1$H NMR (400 MHz, METHANOL-d4) δ ppm 1.41 (s, 9H) 1.89-2.08 (m, 2H) 2.20-2.37 (m, 4H) 2.38-2.57 (m, 2H) 3.27 (s, 3H) 3.94 (br. s., 1H) 4.97-5.15 (m, 1H) 6.60 (d, J=3.71 Hz, 1H) 7.07 (d, J=3.71 Hz, 1H) 8.07 (s, 1H); LCMS (M/Z): 358 (M+H).

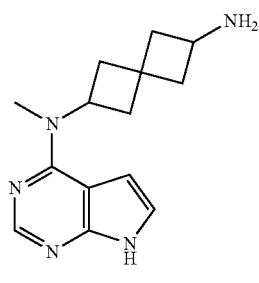 [SMILES: CN(c1ncnc2[nH]ccc12)C1CC2(CC(N)C2)C1]

Intermediate 3: N2-methyl-N2-(7H-pyrrolo[2,3-d]pyrimidin-4-yl)spiro[3.3]heptane-2,6-diamine To a 40-mL vial containing tert-butyl N-[2-[methyl(7H-pyrrolo[2,3-d]pyrimidin-4-yl)amino]spiro[3.3]heptan-6-yl] carbamate (~18 mg, 0.05 mmol) was added MeOH (0.5 mL) followed by 4M HCl in dioxane (1 mL). The mixture was stirred at RT for 1 h. After concentration, it gave the product as a white solid (~13 mg, ~89%). LCMS (M/Z): 258 (M+H). The mixture was used directly without purification.

N-[2-[methyl(7H-pyrrolo[2,3-d]pyrimidin-4-yl)amino] spiro[3.3]heptan-6-yl]benzenesulfonamide 11. To a 40-mL vial containing N2-methyl-N2-(7H-pyrrolo[2,3-d]pyrimidin-4-yl)spiro[3.3]heptane-2,6-diamine (~13 mg, 0.051 mmol) was added DMF (1.5 mL), DMAP (~6.1 mg, 0.050 mmol), DIPEA (~87 ul, 0.50 mmol), and PhSO$_2$Cl (~13 mg in 0.13 mL DMF, 0.075 mmol). The mixture was stirred at room temperature for 30 minutes, monitoring by LCMS. After an additional 30 min, the mixture was treated with water (0.2 mL), DIPEA was removed in vacuo, and the remaining DMF solution was chromatographed on an C$_{18}$ ISCO column (50 g), eluting with MeOH and water. After concentration and lyophilization, it gave the product as a white solid (~11 mg, 52%). $^1$H NMR (400 MHz, METHANOL-d4) δ ppm 1.75-1.95 (m, 2H) 2.01-2.41 (m, 6H) 3.22 (s, 3H) 3.66 (t, J=8.00 Hz, 1H) 4.91-5.04 (m, 1H) 6.56 (d, J=3.51 Hz, 1H) 7.05 (d, J=3.51 Hz, 1H) 7.50-7.68 (m, 3H) 7.80-7.88 (m, 2H) 8.04 (s, 1H); LCMS (M/Z): 398 (M+H).

By proceeding in a similar manner, the following compounds were prepared.

Example 12

Compound 12: 2-chloro-N-[2-[methyl(7H-pyrrolo[2,3-d]pyrimidin-4-yl)amino]spiro[3.3]heptan-6-yl] benzenesulfonamide

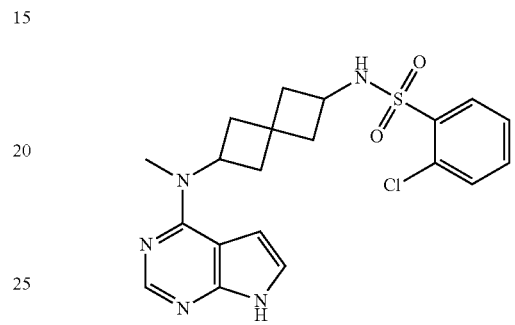

2-chloro-N-[2-[methyl(7H-pyrrolo[2,3-d]pyrimidin-4-yl) amino]spiro[3.3]heptan-6-yl]benzenesulfonamide 12: $^1$H NMR (400 MHz, METHANOL-d4) δ ppm 1.94-2.09 (m, 3H) 2.12-2.37 (m, 5H) 3.21 (s, 3H) 3.65 (quin, J=8.20 Hz, 1H) 4.90-5.03 (m, 1H) 6.56 (d, J=3.51 Hz, 1H) 7.05 (d, J=3.51 Hz, 1H) 7.42-7.53 (m, 1H) 7.58 (d, J=3.71 Hz, 2H) 8.00-8.09 (m, 2H); LCMS (M/Z): 432 (M+H).

Example 13

Compound 13: 4-chloro-N-[2-[methyl(7H-pyrrolo[2,3-d]pyrimidin-4-yl)amino]spiro[3.3]heptan-6-yl] benzenesulfonamide

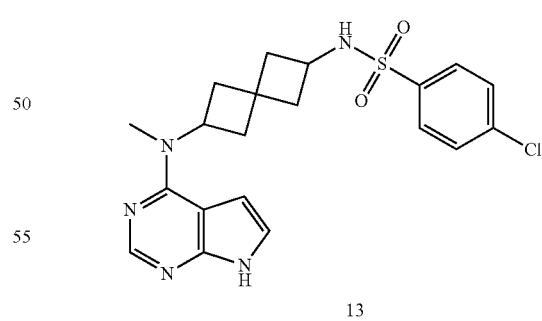

4-chloro-N-[2-[methyl(7H-pyrrolo[2,3-d]pyrimidin-4-yl) amino]spiro[3.3]heptan-6-yl]benzenesulfonamide 13: $^1$H NMR (400 MHz, METHANOL-d4) δ ppm 1.73-1.96 (m, 2H) 2.04-2.28 (m, 4H) 2.28-2.42 (m, 2H) 3.22 (s, 3H) 3.67 (quin, J=8.15 Hz, 1H) 4.91-5.06 (m, 1H) 6.56 (d, J=3.71 Hz, 1H) 7.06 (d, J=3.51 Hz, 1H) 7.57 (d, J=8.59 Hz, 2H) 7.81 (d, J=8.59 Hz, 2H) 8.04 (s, 1H); LCMS (M/Z): 432 (M+H).

Example 14

Compound 14: N-[2-[methyl(7H-pyrrolo[2,3-d]pyrimidin-4-yl)amino]spiro[3.3]heptan-6-yl]-4-(trifluoromethyl)benzenesulfonamide

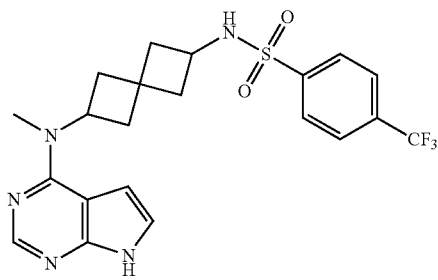

14

N-[2-[methyl(7H-pyrrolo[2,3-d]pyrimidin-4-yl)amino]spiro[3.3]heptan-6-yl]-4-(trifluoromethyl)benzenesulfonamide 14: $^1$H NMR (400 MHz, METHANOL-d4) δ ppm 1.79-1.97 (m, 2H) 2.07-2.29 (m, 4H) 2.29-2.42 (m, 2H) 3.22 (s, 3H) 3.72 (quin, J=8.15 Hz, 1H) 4.92-5.04 (m, 1H) 6.57 (d, J=3.71 Hz, 1H) 7.05 (d, J=3.51 Hz, 1H) 7.88 (d, J=8.20 Hz, 2H) 7.99-8.07 (m, 3H); LCMS (M/Z): 466 (M+H).

Example 15

Compound 15: N-[2-[methyl(7H-pyrrolo[2,3-d]pyrimidin-4-yl)amino]spiro[3.3]heptan-6-yl]methanesulfonamide Scheme 3 (Example 15 as Illustrative):

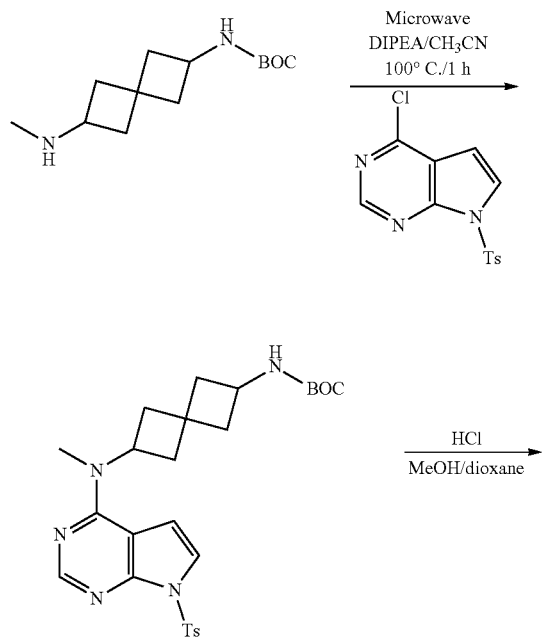

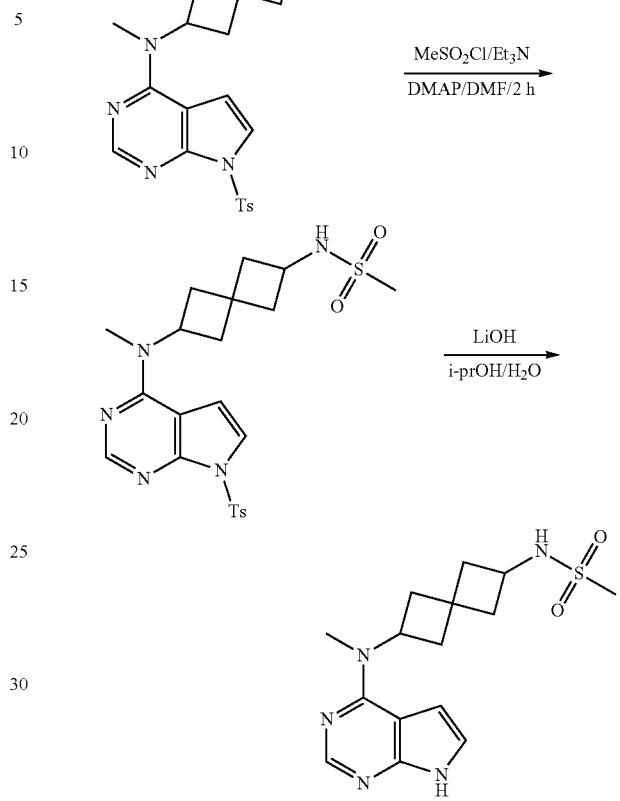

Intermediate 1: tert-butyl N-[2-[methyl-[7-(p-tolylsulfonyl)pyrrolo[2,3-d]pyrimidin-4-yl]amino]spiro[3.3]heptan-6-yl]carbamate To a microwave vial were added tert-butyl N-[6-(methylamino)spiro[3.3]heptan-2-yl]carbamate (0.48 g, 2.0 mmol, crude), 4-chloro-7-(p-tolylsulfonyl)pyrrolo[2,3-d]pyrimidine (0.61 g, 2.0 mmol), DIPEA (0.5 mL), and CH$_3$CN (5 mL). The mixture was heated at 100° C. for 1 hour in microwave (75 W and 250 psi). Then it was cooled to room temperature. After removal of solvent, it was purified by silica ISCO column and eluted with DCM and MeOH. After concentration, it gave an off white solid (~0.64 g, 62.7%). LCMS (M/Z): 512 (M+H).

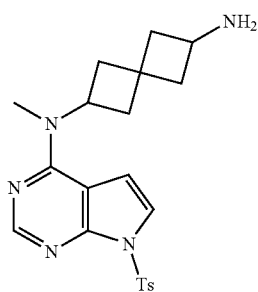 [SMILES: Cc1ccc(S(=O)(=O)n2ccc3c(N(C)C4CC5(CC(N)C5)C4)ncnc32)cc1]

Intermediate 2: N2-methyl-N2-[7-(p-tolylsulfonyl)pyrrolo[2,3-d]pyrimidin-4-yl]spiro[3.3]heptane-2,6-diamine To a 40-mL vial containing tert-butyl N-[2-[methyl-[7-(p-tolylsulfonyl)pyrrolo[2,3-d]pyrimidin-4-yl]amino]spiro[3.3]heptan-6-yl]carbamate (~1.24 g, 2.2 mmol) was added MeOH (1 mL) followed by 4M HCl in dioxane (4 mL). The mixture was stirred at room temperature for 1 hour. After concentration, it gave the product as a light yellow solid (1.12 g, ~100%). LCMS (M/Z): 412 (M+H). The mixture was used directly without purification.

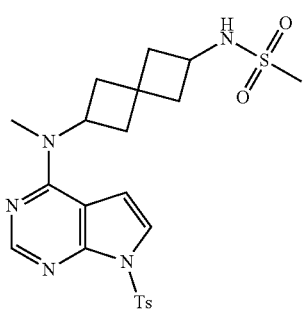 [SMILES: Cc1ccc(S(=O)(=O)n2ccc3c(N(C)C4CC5(CC(NS(C)(=O)=O)C5)C4)ncnc32)cc1]

Intermediate 3: N-[2-[methyl-[7-(p-tolylsulfonyl)pyrrolo[2,3-d]pyrimidin-4-yl]amino]spiro[3.3]heptan-6-yl]methanesulfonamide To a 40-mL vial containing N2-methyl-N2-[7-(p-tolylsulfonyl)pyrrolo[2,3-d]pyrimidin-4-yl]spiro[3.3]heptane-2,6-diamine (~20 mg, 0.05 mmol) was added DCM (1.5 mL), DMAP (~6.1 mg, 0.05 mmol), DIPEA (~87 ul, 0.05 mmol), and MeSO₂Cl (2 drops). The mixture was stirred at room temperature for 2 hours. After removal of solvent, the crude material (~20 mg, ~100%) was directly used for next step. LCMS (M/Z): 490 (M+H).

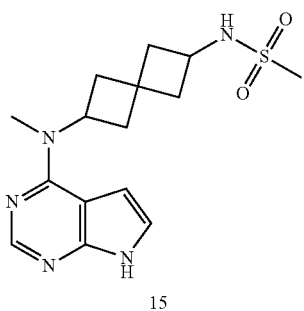 [SMILES: CN(c1ncnc2[nH]ccc12)C1CC2(CC(NS(C)(=O)=O)C2)C1]

15

N-[2-[methyl(7H-pyrrolo[2,3-d]pyrimidin-4-yl)amino]spiro[3.3]heptan-6-yl]methanesulfonamide 15. To a solution of the sulfonamide (~20 mg, ~0.05 mmol) in isopropanol (1 mL) and water (1 mL) was added LiOH.H₂O (42 mg, 1 mmol). The mixture was stirred at 50-55° C. for 2 hours and room temperature for overnight. After the removal of the solvent, it was purified by C18 ISCO column (50 g) and eluted with MeOH and water. After concentration, it gave a white solid (1.5 mg, 9.0%). ¹H NMR (400 MHz, METHANOL-d4) δ ppm 1.20 (d, J=6.83 Hz, 1H) 2.00-2.15 (m, 2H) 2.20-2.52 (m, 5H) 2.55-2.67 (m, 1H) 2.87 (s, 3H) 3.75-3.86 (m, 1H) 4.99-5.15 (m, 1H) 6.61 (d, J=3.71 Hz, 1H) 7.08 (d, J=3.71 Hz, 1H) 8.07 (s, 1H); LCMS (M/Z): 336 (M+H).

By proceeding in a similar manner, the following compounds were prepared.

Example 16

Compound 16: N-[2-[methyl(7H-pyrrolo[2,3-d]pyrimidin-4-yl)amino]spiro[3.3]heptan-6-yl]ethanesulfonamide

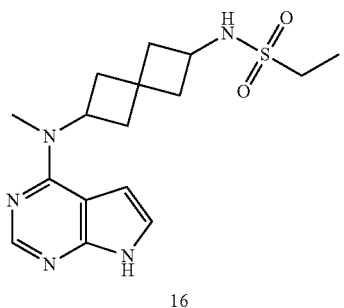 [SMILES: CCS(=O)(=O)NC1CC2(C1)CC(N(C)c1ncnc3[nH]ccc13)C2]

16

N-[2-[methyl(7H-pyrrolo[2,3-d]pyrimidin-4-yl)amino]spiro[3.3]heptan-6-yl]ethanesulfonamide 16. ¹H NMR (400 MHz, METHANOL-d4) δ ppm 1.29 (t, J=7.42 Hz, 3H) 2.01-2.15 (m, 2H) 2.23-2.48 (m, 5H) 2.53-2.66 (m, 1H) 2.97 (q, J=7.42 Hz, 2H) 3.22-3.28 (m, 3H) 3.73-3.82 (m, 1H) 5.02-5.11 (m, 1H) 6.61 (d, J=3.51 Hz, 1H) 7.08 (d, J=3.51 Hz, 1H) 8.07 (s, 1H); LCMS (M/Z): 350 (M+H).

Example 17

Compound 17: N-[2-[methyl(7H-pyrrolo[2,3-d]pyrimidin-4-yl)amino]spiro[3.3]heptan-6-yl]propane-1-sulfonamide

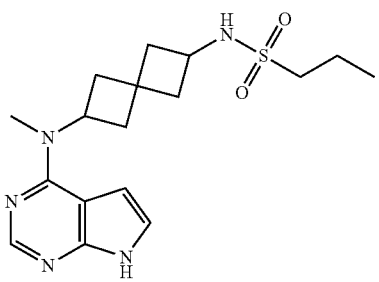

17

N-[2-[methyl(7H-pyrrolo[2,3-d]pyrimidin-4-yl)amino]spiro[3.3]heptan-6-yl]propane-1-sulfonamide 17. $^1$H NMR (400 MHz, METHANOL-d4) δ ppm 1.04 (t, J=7.42 Hz, 3H) 1.72-1.82 (m, 2H) 2.01-2.15 (m, 2H) 2.23-2.48 (m, 5H) 2.56-2.63 (m, 1H) 2.91-2.97 (m, 2H) 3.22-3.27 (m, 3H) 3.73-3.82 (m, 1H) 5.02-5.12 (m, 1H) 6.61 (d, J=3.71 Hz, 1H) 7.08 (d, J=3.71 Hz, 1H) 8.07 (s, 1H); LCMS (M/Z): 364 (M+H).

Example 18

Compound 18: N-[2-[methyl(7H-pyrrolo[2,3-d]pyrimidin-4-yl)amino]spiro[3.3]heptan-6-yl]propane-2-sulfonamide

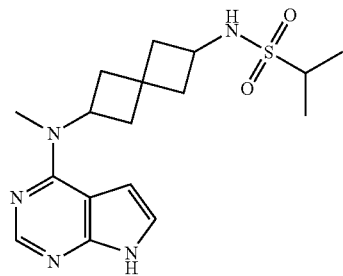

18

N-[2-[methyl(7H-pyrrolo[2,3-d]pyrimidin-4-yl)amino]spiro[3.3]heptan-6-yl]propane-2-sulfonamide 18. $^1$H NMR (400 MHz, METHANOL-d4) δ ppm 1.22-1.36 (m, 6H) 2.08-2.20 (m, 2H) 2.26-2.49 (m, 5H) 2.54-2.72 (m, 1H) 3.04 (s, 1H) 3.12 (quin, J=6.83 Hz, 1H) 3.34-3.47 (m, 1H) 3.71-3.87 (m, 1H) 5.10 (ddd, J=9.45, 7.75, 1.83 Hz, 1H) 6.64 (d, J=3.69 Hz, 1H) 7.11 (d, J=3.42 Hz, 1H) 8.10 (s, 1H); LCMS (M/Z): 364 (M+H).

Example 19

Compound 19: 2-methyl-N-[2-[methyl(7H-pyrrolo[2,3-d]pyrimidin-4-yl)amino]spiro[3.3]heptan-6-yl]propane-1-sulfonamide

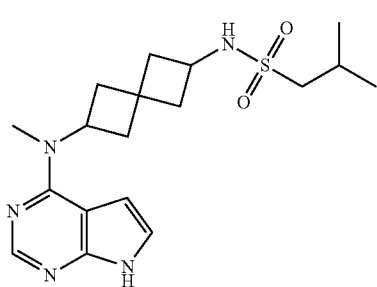

19

2-methyl-N-[2-[methyl(7H-pyrrolo[2,3-d]pyrimidin-4-yl)amino]spiro[3.3]heptan-6-yl]propane-1-sulfonamide 19. $^1$H NMR (400 MHz, METHANOL-d4) δ ppm 1.11 (dd, J=6.83, 0.73 Hz, 6H) 2.06-2.24 (m, 3H) 2.26-2.42 (m, 4H) 2.45-2.51 (m, 1H) 2.63 (ddd, J=10.98, 7.07, 5.61 Hz, 1H) 2.89 (d, J=6.34 Hz, 2H) 3.30-3.31 (m, 3H) 3.77-3.85 (m, 1H) 5.06-5.14 (m, 1H) 6.64 (d, J=3.66 Hz, 1H) 7.11 (d, J=3.42 Hz, 1H) 8.10 (s, 1H); LCMS (M/Z): 378 (M+H).

Example 20

Compound 20: N-[2-[methyl(7H-pyrrolo[2,3-d]pyrimidin-4-yl)amino]spiro[3.3]heptan-6-yl]cyclopentanesulfonamide

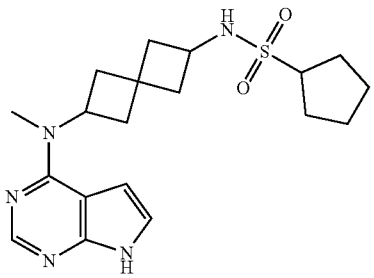

20

N-[2-[methyl(7H-pyrrolo[2,3-d]pyrimidin-4-yl)amino]spiro[3.3]heptan-6-yl]cyclopentanesulfonamide 20. $^1$H NMR (400 MHz, METHANOL-d4) δ ppm 1.59-1.73 (m, 2H) 1.73-1.84 (m, 2H) 1.88-2.05 (m, 4H) 2.05-2.21 (m, 3H) 2.27-2.42 (m, 4H) 2.44-2.50 (m, 1H) 2.55-2.71 (m, 2H) 3.27-3.31 (m, 3H) 3.34-3.40 (m, 1H) 3.40-3.51 (m, 1H) 3.79-3.87 (m, 1H) 5.05-5.15 (m, 1H) 6.61-6.67 (m, 1H) 7.11 (d, J=3.66 Hz, 1H) 8.08-8.12 (m, 1H); LCMS (M/Z): 390 (M+H).

Example 21

Compound 21: 3,3,3-trifluoro-N-[2-[methyl(7H-pyrrolo[2,3-d]pyrimidin-4-yl)amino]spiro[3.3]heptan-6-yl]propane-1-sulfonamide

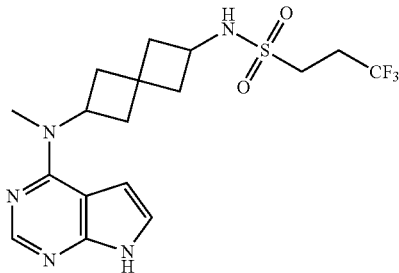

21

3,3,3-trifluoro-N-[2-[methyl(7H-pyrrolo[2,3-d]pyrimidin-4-yl)amino]spiro[3.3]heptan-6-yl]propane-1-sulfonamide 21. $^1$H NMR (400 MHz, METHANOL-d4) δ ppm 2.04-2.18 (m, 2H) 2.27-2.44 (m, 4H) 2.47-2.52 (m, 1H) 2.59-2.71 (m, 3H) 3.17-3.28 (m, 2H) 3.30-3.31 (m, 3H) 3.81-3.89 (m, 1H) 5.06-5.15 (m, 1H) 6.64 (d, J=3.66 Hz, 1H) 7.11 (d, J=3.42 Hz, 1H) 8.10 (s, 1H); LCMS (M/Z): 418 (M+H).

Example 22
Compound 22: N-((6-(methyl(7H-pyrrolo[2,3-d]pyrimidin-4-yl)amino)spiro[3.3]heptan-2-yl)methyl)methanesulfonamide
Scheme 4 (Example 22 as Illustrative):
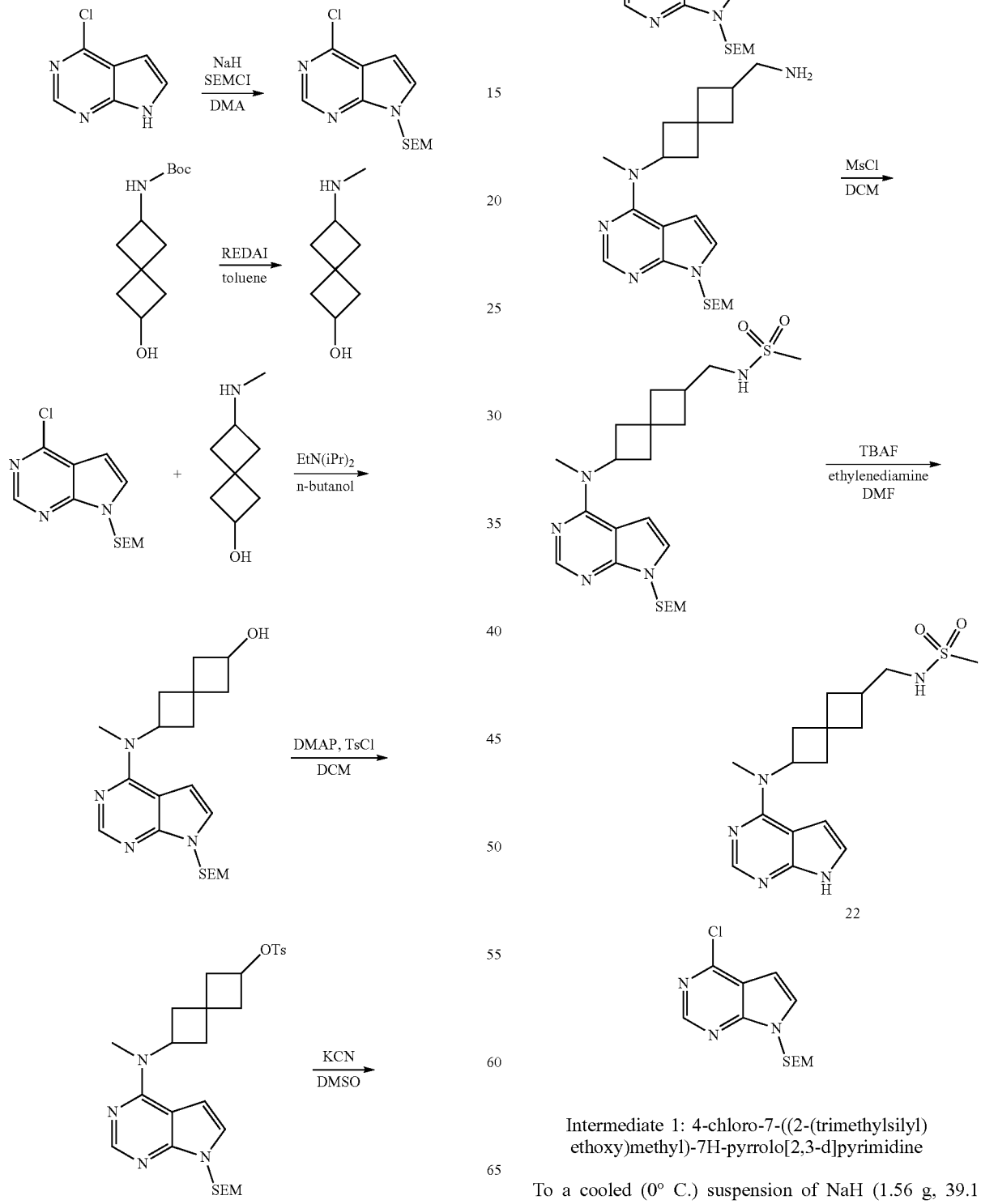
Intermediate 1: 4-chloro-7-((2-(trimethylsilyl)ethoxy)methyl)-7H-pyrrolo[2,3-d]pyrimidine
To a cooled (0° C.) suspension of NaH (1.56 g, 39.1 mmol, 60% in mineral oil) in DMA (40 mL) was cannulated a solution of 4-chloro-7H-pyrrolo[2,3-d]pyrimidine (5.00 g, 32.6 mmol) in DMA (40 mL) at a rate that modulated excessive gas formation. After cannulation was completed, the reaction stirred in ice bath for 30 minutes before a solution of SEMCl (6.92 mL, 39.1 mmol) in DMA (20 mL) was added dropwise. After dropwise addition was completed, the reaction was removed from the ice bath and allowed to stir at room temp for 1 h. The reaction was slowly poured into water (100 mL) and the mixture extracted with 3×150 mL EtOAc. The combined organic fractions were washed 1×100 mL sat. aq. NaCl, dried with $Na_2SO_4$, filtered, and concentrated in vacuo. The resultant residue was chromatographed on silica gel (330 g Isco column, 0 to 25% EtOAc in heptane over 35.4 min.) to give 8.23 g (89%) of 4-chloro-7-((2-(trimethylsilyl)ethoxy)methyl)-7H-pyrrolo[2,3-d]pyrimidine as a colorless oil. $^1$H NMR (400 MHz, DMSO-$d_6$) δ=8.66 (s, 1H), 7.85 (d, J=3.7 Hz, 1H), 6.69 (d, J=3.7 Hz, 1H), 5.62 (s, 2H), 3.52-3.46 (m, 2H), 0.82-0.75 (m, 2H), −0.12--0.16 (m, 9H). LC/MS RT=1.49 min., 284.2 [M+H]+.

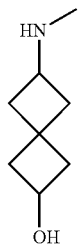

Intermediate 2:
6-(methylamino)spiro[3.3]heptan-2-ol

To a cooled (13° C.) suspension of tert-butyl (6-hydroxyspiro[3.3]heptan-2-yl)carbamate (2.50 g, 11.0 mmol) in toluene (26 mL) in a 0.25 L 3 neck round bottom flask equipped with a reflux condenser, $N_2$ line, septum and thermowell, was added a solution of REDAl (19.0 mL, 68.4 mmol, 3.60 molar) in toluene dropwise over 25 min while maintaining the internal temperature below 30° C. After addition was completed, the reaction was heated to reflux for 1 h before it was cooled to 2° C. The reaction was quenched with the slow addition of saturated aq. $Na_2SO_4$ (40 mL). The resultant mixture was filtered on a Buchner funnel and solids rinsed with 10 mL DCM. The organic layer was separated and the aq. layer extracted with 4×20 mL DCM. The combined organic fractions were dried with $MgSO_4$, filtered, and concentrated in vacuo to give 1.08 g (70%) of 6-(methylamino)spiro[3.3]heptan-2-ol as a colorless oil. $^1$H NMR (400 MHz, METHANOL-$d_4$) δ=4.08 (quin, J=7.4 Hz, 1H), 3.10-2.98 (m, 1H), 2.43-2.34 (m, 1H), 2.31-2.12 (m, 6H), 1.95-1.84 (m, 2H), 1.77 (td, J=8.4, 10.9 Hz, 2H). LC/MS RT=1.49 min., 284.2 [M+H]+.

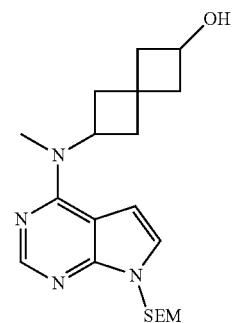

Intermediate 3: 6-(methyl(7-((2-(trimethylsilyl)ethoxy)methyl)-7H-pyrrolo[2,3-d]pyrimidin-4-yl)amino)spiro[3.3]heptan-2-ol A mixture of 4-chloro-7-((2-(trimethylsilyl)ethoxy)methyl)-7H-pyrrolo[2,3-d]pyrimidine (2.17 g, 7.65 mmol), 6-(methylamino)spiro[3.3]heptan-2-ol (1.08 g, 7.65 mmol) and EtN(i-Pr)$_2$ (4.00 mL, 22.9 mmol) in n-butanol (15 mL) was heated to 110° C. for 18 h. The solution was cooled to room temp., concentrated in vacuo and the resultant residue was chromatographed on silica gel (120 g Isco column, 0 to 100% EtOAc in heptane over 36 min. then 100% EtOAc for 10 min.) to give 1.30 g (44%) of 6-(methyl(7-((2-(trimethylsilyl)ethoxy)methyl)-7H-pyrrolo[2,3-d]pyrimidin-4-yl)amino)spiro[3.3]heptan-2-ol as a tan solid. $^1$H NMR (400 MHz, DMSO-$d_6$) δ=8.13 (s, 1H), 7.29 (d, J=3.7 Hz, 1H), 6.61 (d, J=3.7 Hz, 1H), 5.47 (s, 2H), 5.16-5.05 (m, 1H), 4.90 (d, J=6.4 Hz, 1H), 4.03-3.93 (m, 1H), 3.48-3.42 (m, 2H), 3.18 (s, 3H), 2.44-2.36 (m, 1H), 2.26-2.16 (m, 4H), 2.16-2.08 (m, 1H), 1.91-1.79 (m, 2H), 0.82-0.75 (m, 2H), −0.08--0.14 (m, 9H). LC/MS RT=0.90 min., 389.2 [M+H]$^+$.

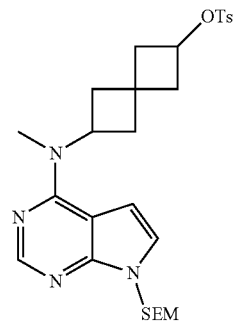 [SMILES: Cc1ccc(S(=O)(=O)OC2CC3(C2)CC(N(C)c2ncnc4c2ccn4COCC[Si](C)(C)C)C3)cc1]

Intermediate 4: 6-(methyl(7-((2-(trimethylsilyl)ethoxy)methyl)-7H-pyrrolo[2,3-d]pyrimidin-4-yl)amino)spiro[3.3]heptan-2-yl 4-methylbenzenesulfonate To a solution of 6-(methyl(7-((2-(trimethylsilyl)ethoxy)methyl)-7H-pyrrolo[2,3-d]pyrimidin-4-yl)amino)spiro[3.3]heptan-2-ol (1.30 g, 3.35 mmol), DMAP (82.0 mg, 0.669 mmol) and NEt$_3$ (1.50 mL, 10.7 mmol) in DCM (17 mL) was added TsCl (1.08 g, 5.69 mmol). Reaction stirred at room temp for 16 h before the reaction was poured into water (15 mL). The organic layer was separated and the aqueous layer was extracted 3×10 mL EtOAc. The combined organic layers were washed 1×10 mL saturated aq.

NaHCO$_3$, 1×10 mL saturated aq. NaCl, dried with Na$_2$SO$_4$, filtered and concentrated in vacuo. The resultant residue was chromatographed on silica gel (40 g Isco column, 0 to 75% EtOAc in heptane over 19 min.) to give 1.70 g (94%) of 6-(methyl(7-((2-(trimethylsilyl)ethoxy)methyl)-7H-pyrrolo[2,3-d]pyrimidin-4-yl)amino)spiro[3.3]heptan-2-yl 4-methylbenzenesulfonate as a brown oil. $^1$H NMR (400 MHz, DMSO-d$_6$) δ=8.12 (s, 1H), 7.76 (d, J=8.4 Hz, 2H), 7.46 (d, J=8.2 Hz, 2H), 7.28 (d, J=3.7 Hz, 1H), 6.60 (d, J=3.7 Hz, 1H), 5.46 (s, 2H), 5.04 (t, J=8.1 Hz, 1H), 4.77-4.66 (m, 1H), 3.48-3.41 (m, 2H), 3.14 (s, 3H), 2.45-2.39 (m, 4H), 2.29-2.09 (m, 6H), 2.05 (dd, J=7.5, 12.0 Hz, 1H), 0.81-0.75 (m, 2H), −0.10−−0.14 (m, 9H). LC/MS RT=1.55 min., 543.2 [M+H]$^+$.

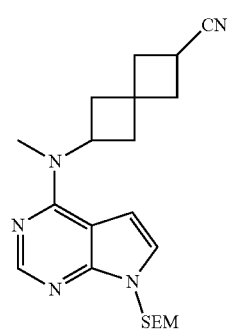 [SMILES: CN(c1ncnc2c1ccn2COCC[Si](C)(C)C)C1CC2(CC(C#N)C2)C1]

Intermediate 5: 6-(methyl(7-((2-(trimethylsilyl)ethoxy)methyl)-7H-pyrrolo[2,3-d]pyrimidin-4-yl)amino)spiro[3.3]heptane-2-carbonitrile A mixture of 6-(methyl(7-((2-(trimethylsilyl)ethoxy)methyl)-7H-pyrrolo[2,3-d]pyrimidin-4-yl)amino)spiro[3.3]heptan-2-yl 4-methylbenzenesulfonate (0.300 g, 0.553 mmol) and KCN (108 mg, 1.66 mmol) was diluted with anhydrous DMSO (2 mL) and the reaction heated to 90° C. for 27 h. The reaction was allowed to cool to room temperature, poured into water (10 mL), and extracted 4×5 mL EtOAc. The combined organic fractions were washed 1×3 mL water, 1×3 mL saturated aq. NaCl, dried with Na$_2$SO$_4$, filtered, and concentrated in vacuo. The resultant residue was chromatographed on silica gel (24 g Isco column, 0 to 100% EtOAc in heptane over 15 min.) to give 115 mg (52%) of 6-(methyl(7-((2-(trimethylsilyl)ethoxy)methyl)-7H-pyrrolo[2,3-d]pyrimidin-4-yl)amino)spiro[3.3]heptane-2-carbonitrile as a tan solid. $^1$H NMR (400 MHz, DMSO-d$_6$) δ=8.14 (s, 1H), 7.30 (d, J=3.7 Hz, 1H), 6.63 (d, J=3.7 Hz, 1H), 5.47 (s, 2H), 5.12-5.01 (m, 1H), 3.48-3.42 (m, 2H), 3.24 (t, J=8.4 Hz, 1H), 3.18 (s, 3H), 2.57-2.50 (m, 1H), 2.44-2.21 (m, 7H), 0.81-0.76 (m, 2H), −0.12 (s, 9H). LC/MS RT=1.09 min., 398.3 [M+H]$^+$.

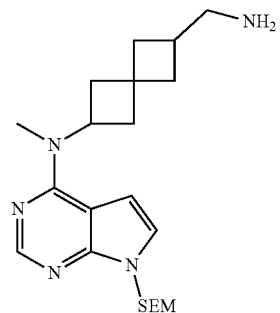 [SMILES: CN(c1ncnc2c1ccn2COCC[Si](C)(C)C)C1CC2(CC(CN)C2)C1]

Intermediate 6: N-(6-(aminomethyl)spiro[3.3]heptan-2-yl)-N-methyl-7-((2-(trimethylsilyl)ethoxy)methyl)-7H-pyrrolo[2,3-d]pyrimidin-4-amine To a cooled (0° C.) solution of 6-(methyl(7-((2-(trimethylsilyl)ethoxy)methyl)-7H-pyrrolo[2,3-d]pyrimidin-4-yl)amino)spiro[3.3]heptane-2-carbonitrile (115 mg, 0.289 mmol) in THF (2.4 mL) was added LAH (27 mg, 0.72 mmol). The reaction was stirred 2 h at 0° C. before it was quenched with Na$_2$SO$_4$.10H$_2$O (350 mg, added in portions). Stirring continued until no gas evolution was observed and the mixture was diluted with DCM (10 mL) and filtered through celite on a Buchner funnel. The mother liquor was concentrated in vacuo to give 115 mg of N-(6-(aminomethyl)spiro[3.3]heptan-2-yl)-N-methyl-7-((2-(trimethylsilyl)ethoxy)methyl)-7H-pyrrolo[2,3-d]pyrimidin-4-amine as a colorless oil, which was used without further purification. $^1$H NMR (400 MHz, METHANOL-d$_4$) 6=8.13 (s, 1H), 7.19 (d, J=3.7 Hz, 1H), 6.67 (d, J=3.7 Hz, 1H), 5.53 (s, 2H), 5.04 (quin, J=8.5 Hz, 1H), 3.54-3.48 (m, 2H), 3.27 (s, 3H), 2.63 (d, J=6.8 Hz, 2H), 2.48-2.40 (m, 1H), 2.33-2.24 (m, 4H), 2.15-2.06 (m, 1H), 1.74 (dd, J=6.8, 12.1 Hz, 1H), 1.61-1.53 (m, 2H), 0.87-0.80 (m, 2H), −0.08−−0.12 (m, 9H). LC/MS RT=0.61 min., 402.2 [M+H]$^+$.

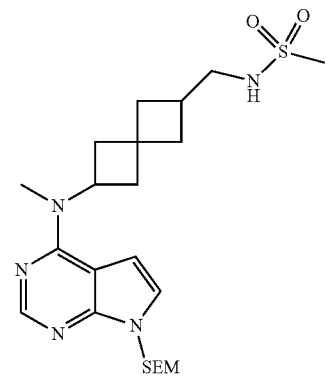

Intermediate 7: N-((6-(methyl(7-((2-(trimethylsilyl)ethoxy)methyl)-7H-pyrrolo[2,3-d]pyrimidin-4-yl)amino)spiro[3.3]heptan-2-yl)methyl)methanesulfonamide To a solution of N-(6-(aminomethyl)spiro[3.3]heptan-2-yl)-N-methyl-7-((2-(trimethylsilyl)ethoxy)methyl)-7H-pyrrolo[2,3-d]pyrimidin-4-amine (57 mg, 0.14 mmol) and NEt$_3$ (59 mL, 0.43 mmol) in DCM (1.4 mL) was added methane sulfonylchloride (13 mL, 0.17 mmol). The reaction was stirred for 2.75 h before it was concentrated in vacuo and the residue chromatographed on silica gel (12 g Isco column, 0 to 100% EtOAc in heptane over 16 min.) to give 38 mg (56%) of N-((6-(methyl(7-((2-(trimethylsilyl)ethoxy)methyl)-7H-pyrrolo[2,3-d]pyrimidin-4-yl)amino)spiro[3.3]heptan-2-yl)methyl)methanesulfonamide as a white solid. $^1$H NMR (400 MHz, METHANOL-$d_4$) δ=8.14 (s, 1H), 7.21 (d, J=3.7 Hz, 1H), 6.69 (d, J=3.7 Hz, 1H), 5.53 (s, 2H), 5.06-4.95 (m, 1H), 3.55-3.48 (m, 2H), 3.27 (s, 3H), 3.05 (d, J=7.2 Hz, 2H), 2.92-2.87 (m, 3H), 2.49-2.36 (m, 2H), 2.35-2.25 (m, 4H), 2.11 (ddd, J=3.5, 8.0, 11.5 Hz, 1H), 1.95-1.78 (m, 2H), 0.87-0.81 (m, 2H), −0.07−−0.11 (m, 9H). LC/MS RT=1.08 min., 480.2 [M+H]$^+$.

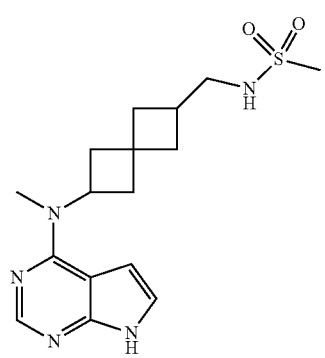

N-((6-(methyl(7H-pyrrolo[2,3-d]pyrimidin-4-yl)amino)spiro[3.3]heptan-2-yl)methyl)methanesulfonamide 22. To a solution of N-((6-(methyl(7-((2-(trimethylsilyl)ethoxy)methyl)-7H-pyrrolo[2,3-d]pyrimidin-4-yl)amino)spiro[3.3]heptan-2-yl)methyl)methanesulfonamide (38 mg, 0.079 mmol) in DMF (1 mL) was added ethylene diamine (11 mL, 0.16 mmol) and a solution of TBAF (0.16 mL, 0.16 mmol, 1 molar) in THF. The reaction was heated to 60° C. for 24 h before additional TBAF (0.32 mL, 0.32 mmol, 1 molar) in THF was added. The temperature of the reaction was increased to 90° C. and stirred an additional 72 h before the solution was concentrated in vacuo and resultant residue chromatographed on a $C_{18}$ reverse phase column (43 g $C_{18}$ Isco column 100% water 1 min., then 0 to 100% MeOH in water over 15 min.) to give 18 mg (64%) of N-((6-(methyl(7H-pyrrolo[2,3-d]pyrimidin-4-yl)amino)spiro[3.3]heptan-2-yl)methyl)methanesulfonamide 22 as a white solid. $^1$H NMR (400 MHz, METHANOL-$d_4$) δ=8.07 (s, 1H), 7.07 (d, J=3.7 Hz, 1H), 6.60 (d, J=3.7 Hz, 1H), 5.05 (quin, J=8.6 Hz, 1H), 3.27 (s, 3H), 3.05 (d, J=7.2 Hz, 2H), 2.90 (s, 3H), 2.48-2.36 (m, 2H), 2.34-2.24 (m, 4H), 2.11 (ddd, J=3.4, 8.1, 11.6 Hz, 1H), 1.92 (dd, J=7.4, 10.9 Hz, 1H), 1.82 (dd, J=7.7, 11.8 Hz, 1H). LC/MS RT=0.32 min., 350.2 [M+H]$^+$ By proceeding in a similar manner the following compounds were prepared.

Example 23

Compound 23: N-((6-(methyl(7H-pyrrolo[2,3-d]pyrimidin-4-yl)amino)spiro[3.3]heptan-2-yl)methyl)ethanesulfonamide

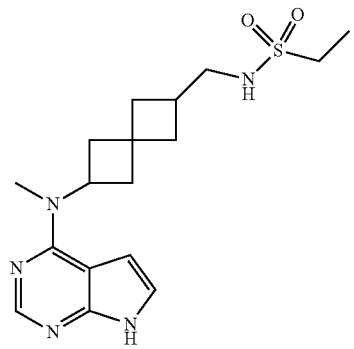

N-((6-(methyl(7H-pyrrolo[2,3-d]pyrimidin-4-yl)amino)spiro[3.3]heptan-2-yl)methyl)ethanesulfonamide 23. $^1$H NMR (400 MHz, METHANOL-$d_4$) δ=8.07 (s, 1H), 7.07 (d, J=3.7 Hz, 1H), 6.60 (d, J=3.5 Hz, 1H), 5.05 (quin, J=8.6 Hz, 1H), 3.27 (s, 3H), 3.06-2.98 (m, 4H), 2.47-2.36 (m, 2H), 2.35-2.24 (m, 4H), 2.11 (ddd, J=3.7, 8.1, 11.5 Hz, 1H), 1.91 (dd, J=7.3, 10.8 Hz, 1H), 1.81 (dd, J=7.5, 11.6 Hz, 1H), 1.29 (t, J=7.3 Hz, 3H). LC/MS RT=0.39 min., 364.2 [M+H]$^+$.

Example 24

Compound 24: N-methyl-6-[methyl(9H-purin-6-yl)amino]spiro[3.3]heptane-2-sulfonamide Scheme 5 (Example 24 as Illustrative)

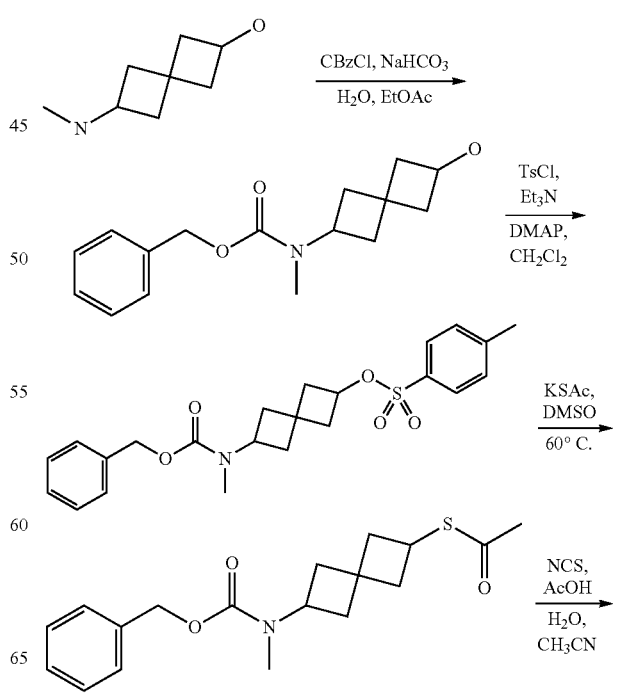

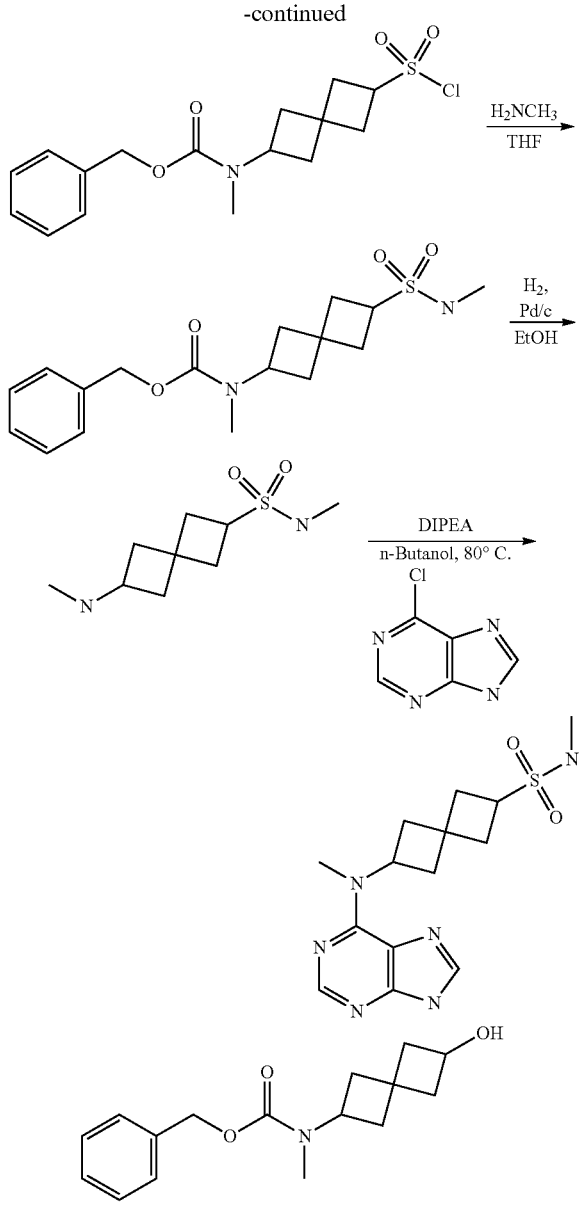

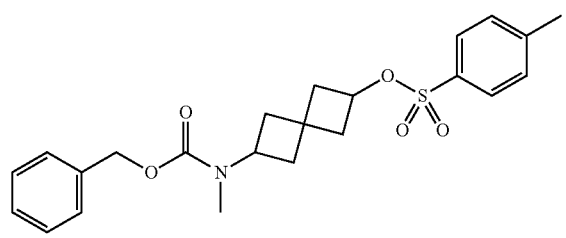 [SMILES: Cc1ccc(S(=O)(=O)OC2CC3(C2)CC(N(C)C(=O)OCc2ccccc2)C3)cc1]

Intermediate 2: [6-[Benzyloxycarbonyl(methyl)amino]spiro[3.3]heptan-2-yl] 4-methylbenzenesulfonate p-Toluenesulfonyl chloride (2.09 g, 11.0 mmol) was added to a stirred solution of benzyl N-(2-hydroxyspiro[3.3]heptan-6-yl)-N-methyl-carbamate (2.35 g, 8.55 mmol), triethylamine (2.66 mL, 19.1 mmol), DMAP (233 mg, 1.91 mmol), and $CH_2Cl_2$ (35 mL). The reaction mixture was stirred for 18 hours before the solution was poured into water (50 mL), and the layers were separated. The aqueous layer was extracted with EtOAc (2×50 mL). The organic layers were combined, washed with brine (1×50 mL), dried ($Na_2SO_4$), filtered, concentrated, and purified by silica gel chromatography, employing a gradient of 0 to 75% EtOAc in heptane to provide the title compound as a colorless oil (3.14 g, 86%). $^1$H NMR (400 MHz, CHLOROFORM-d): δ ppm 2.17-2.34 (m, 3H), 2.37-2.64 (m, 6H), 2.78 (d, J=5.27 Hz, 3H), 3.18 (s, 3H), 3.74 (quin, J=8.30 Hz, 1H), 3.95 (q, J=5.08 Hz, 1H), 4.94-5.06 (m, 1H), 6.59 (d, J=4.10 Hz, 1H), 7.27 (s, 2H), 7.44 (d, J=4.10 Hz, 1H), 8.03 (d, J=8.39 Hz, 2H), 8.37 (s, 1H); m/z 430 [M+H]$^+$.

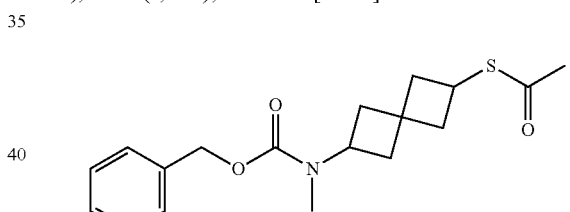

Intermediate 3: S-[6-[Benzyloxycarbonyl(methyl)amino]spiro[3.3]heptan-2-yl] ethanethioate Potassium thioacetate (6.62 g, 58.0 mmol) was added to a stirred solution of [6-[benzyloxycarbonyl(methyl)amino]spiro[3.3]heptan-2-yl] 4-methylbenzenesulfonate (5.00 g, 11.6 mmol) and DMSO (50 mL). The external temperature was raised to 60° C., and the initially heterogeneous solution became homogeneous. After 17 hours at 60° C. the solution was cooled, and the reaction mixture was diluted with EtOAc (50 mL) and aqueous $NaHCO_3$ (75 mL). The layers were separated, and the aqueous layer was extracted with EtOAc (2×50 mL). The organic layers were combined, washed with brine (1×50 mL), dried ($Na_2SO_4$), filtered, concentrated, and purified by silica gel chromatography, employing a gradient of 0 to 40% EtOAc in heptane to provide the title compound as a colorless oil (3.26 g, 84%). $^1$H NMR (400 MHz, CHLOROFORM-d): δ ppm 1.98-2.20 (m, 5H), 2.25 (s, 3H), 2.29-2.44 (m, 2H), 2.56 (ddd, J=11.47, 7.66, 3.90 Hz, 1H), 2.81 (s, 3H), 3.93 (quin, J=8.35 Hz, 1H), 4.15-4.64 (m, 1H), 5.09 (s, 2H), 7.26-7.37 (m, 4H); m/z 334 [M+H]$^+$.

Intermediate 1: Benzyl N-(2-hydroxyspiro[3.3]heptan-6-yl)-N-methyl-carbamate

Benzyl chloroformate (1.50 mL, 10.5 mmol) was added to a stirred solution of 6-(methylamino)spiro[3.3]heptan-2-ol (1.59 g, 10.5 mmol), aqueous sodium carbonate (21.1 mL, 21.1 mmol of a 1N solution), and EtOAc (10.5 mL) at 0° C. After the addition was completed, the ice-water bath was removed, and the reaction mixture was stirred at ambient temperature for 4 hours before the layers were separated, and the aqueous layer was washed with EtOAc (2×10 mL). The organic layers were combined, washed with brine (1×10 mL), dried ($Na_2SO_4$), filtered, and concentrated to a colorless oil (2.46 g, 85%). $^1$H NMR (400 MHz, CHLOROFORM-d): δ ppm 1.91 (dt, J=11.42, 6.98 Hz, 2H), 2.03 (s, 1H), 2.05-2.21 (m, 4H), 2.27 (dt, J=11.66, 5.98 Hz, 1H), 2.43-2.51 (m, 1H), 2.82 (s, 3H), 4.18 (quin, J=7.22 Hz, 1H), 5.10 (s, 2H), 7.31-7.38 (m, 5H); m/z 276 [M+H]$^+$.

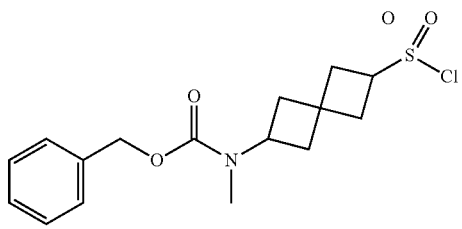

Intermediate 4: Benzyl N-(2-chlorosulfonylspiro[3.3]heptan-6-yl)-N-methyl-carbamate A solution of S-[6-[benzyloxycarbonyl(methyl)amino]spiro[3.3]heptan-2-yl] ethanethioate and acetonitrile (11 mL) was added slowly, dropwise to a stirred solution of NCS (2.87 g, 20.9 mmol), acetic acid:H$_2$O (0.80 mL of a 1:1 solution by volume), and acetonitrile (12 mL) at ambient temperature at such a rate that the internal temperature of the solution did not exceed 30° C. After fifteen minutes the mixture was diluted with EtOAc (80 mL), washed with saturated aqueous NaHCO$_3$ (1×20 mL), washed with brine (1×20 mL), dried (Na$_2$SO$_4$), filtered, concentrated, and purified by silica gel chromatography, employing a gradient of 0 to 40% EtOAc in heptane, to give the title compound as a white solid (1.53 g, 61%). $^1$H NMR (400 MHz, CHLOROFORM-d): 5 ppm 2.17-2.26 (m, 2H), 2.27-2.38 (m, 2H), 2.45 (ddd, J=12.45, 8.74, 3.22 Hz, 1H), 2.57-2.65 (m, 1H), 2.66-2.81 (m, 3H), 2.82 (s, 3H), 4.29 (quin, J=8.20 Hz, 1H), 4.35-4.55 (m, 1H), 5.10 (s, 2H), 7.28-7.38 (m, 6H); m/z 358 [M+H]$^+$.

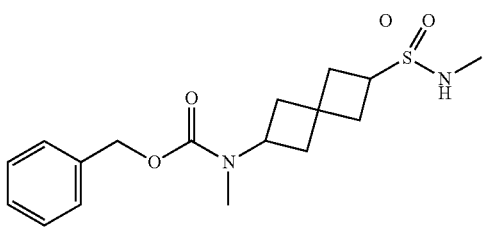

Intermediate 5: Benzyl N-methyl-N-[2-(methylsulfamoyl)spiro[3.3]heptan-6-yl]carbamate Methylamine (10.7 mL, 4.28 mmol of a 2M solution in THF) was added dropwise to a solution of Benzyl N-(2-chlorosulfonylspiro[3.3]heptan-6-yl)-N-methyl-carbamate (1.53 g, 4.28 mmol) and THF (12.2 mL) at 0° C. The reaction mixture was permitted to warm to ambient temperature as it was stirred overnight. After 17 h the solution was poured into water (50 mL) and extracted with EtOAc (3×50 mL). The organic extracts were combined, washed with brine (1×30 mL), dried (Na$_2$SO$_4$), filtered, concentrated, and purified by silica gel chromatography, employing a gradient of 0 to 100% EtOAc in heptane, to give the title compound as a white solid (1.19 g, 79%). $^1$H NMR (400 MHz, CHLOROFORM-d): 5 ppm 2.09-2.17 (m, 2H), 2.18-2.34 (m, 3H), 2.35-2.43 (m, 1H), 2.44-2.55 (m, 2H), 2.76 (d, J=5.47 Hz, 3H), 2.81 (s, 3H), 3.70 (quin, J=8.39 Hz, 1H), 3.97 (q, J=4.95 Hz, 1H), 5.09 (s, 2H), 7.28-7.38 (m, 5H); m/z 353 [M+H]$^+$.

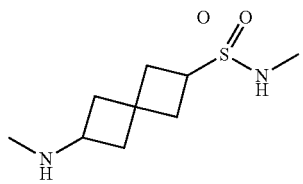

Intermediate 6: N-Methyl-6-(methylamino)spiro[3.3]heptane-2-sulfonamide

A 500 mL round bottom flask that had been flushed with nitrogen was charged with wet 5% Pd/C (700 mg); trace EtOAc was employed to rinse down the neck of the flask. Benzyl N-methyl-N-[2-(methylsulfamoyl)spiro[3.3]heptan-6-yl]carbamate (700 mg, 1.99 mmol) and EtOH (70 mL) were added. Air was evacuated and replaced with hydrogen. After 18 hours the atmosphere was replaced with nitrogen, and the mixture was filtered through a pad of Celite, eluting with copious EtOAc. The filtrate was concentrated to provide the title compound as a white solid (395 mg, 91%). $^1$H NMR (400 MHz, METHANOL-d4): δ ppm 1.78-1.90 (m, 2H), 2.20-2.32 (m, 5H), 2.35-2.48 (m, 4H), 2.65 (s, 3H), 3.05-3.16 (m, 1H), 3.81 (quin, J=8.30 Hz, 1H); m/z 219 [M+H]$^+$.

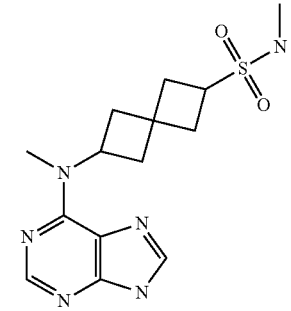

Compound 24: N-methyl-6-[methyl(9H-purin-6-yl)amino]spiro[3.3]heptane-2-sulfonamide In a 5 mL wheaton vial 6-chloro-9H-purine (0.34 mmol, 87.0 mg) and N-methyl-6-(methylamino)spiro[3.3]heptane-2-sulfonamide (0.34 mmol, 52.0 mg) were taken in n-Butanol (3.0 mL). N,N-Diisopropylethylamine (0.29 mL, 1.7 mmol) was added to this. The reaction was stirred at 80° C. for 16 h. Cooled and the reaction was concentrated. The crude was triturated using acetonitrile (2×2.0 mL) to give 67 mg of the product (Purity 85%). This was further purified on preparative HPLC using water/methanol as eluent to give product with 93% purity. LC-MS 337 (M+H); $^1$H-NMR (400 MHz, DMSO-d6) δ ppm 2.11-2.43 (m, 8H) 2.49-2.58 (m, 3H) 3.31-3.36 (m, 2H) 3.69-3.89 (m, 1H) 5.24-6.04 (m, 1H) 6.62-6.93 (m, 1H) 7.88-8.12 (m, 1H) 8.13-8.29 (m, 1H) 11.86-13.35 (m, 1H);

By proceeding in a similar fashion, the following was prepared.

Example 25

Compound 25: N-methyl-6-[methyl(1H-pyrazolo[3,4-d]pyrimidin-4-yl)amino]spiro[3.3]heptane-2-sulfonamide

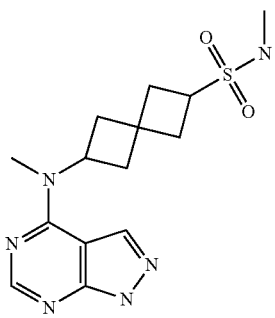

N-methyl-6-[methyl(1H-pyrazolo[3,4-d]pyrimidin-4-yl)amino]spiro[3.3]heptane-2-sulfonamide LC-MS 337 (M+H); $^1$H NMR (400 MHz, DMSO-d6) δ ppm 2.08-2.44 (m, 7H) 2.51-2.58 (m, 3H) 3.17-3.24 (m, 3H) 3.60-3.92 (m, 1H) 4.68-5.48 (m, 1H) 6.40-7.01 (m, 1H) 8.16 (d, J=18.35 Hz, 2H) 12.55-13.69 (m, 1H).

Examples 26 and 27

Compounds 26 and 27: Separation of enantiomers of N-methyl-6-[methyl(7H-pyrrolo[2,3-d]pyrimidin-4-yl)amino]spiro[3.3]heptane-2-sulfonamide The racemic material was dissolved in MeOH. The separation of Enantiomer A and B was carried out on a Chiral Tech Chiralpak IF semi preparative column (30×250 mm, 5 micron) eluted with isocratic solvent (70% EtOH and 30% Hexane). Enantiomer A was collected between 11.1 to 12.1 min. Enantiomer B was collected between 12.7 to 14.1 min. The enantiomers A and B were analyzed on a Chiral Tech Chiralpak IF-3 analytical column (4.6×150 mm, 3 micron) eluted with isocratic solvent (60% EtOH and 40% Hexane).

Compound 26: Enantiomer A: $^1$H NMR (400 MHz, METHANOL-d4) δ ppm 2.30-2.41 (m, 4H) 2.44-2.59 (m, 4H) 2.68 (s, 3H) 3.27 (s, 3H, overlapped with MeOH-d4) 3.87 (quin, J=8.30 Hz, 1H) 5.01-5.10 (m, 1H) 6.61 (d, J=3.71 Hz, 1H) 7.08 (d, J=3.71 Hz, 1H) 8.07 (s, 1H); LCMS (M/Z): 336 (M+H); retention time on Chiralpak IF-3 column: 6.56 min.

Compound 27: Enantiomer B: $^1$H NMR (400 MHz, METHANOL-d4) δ ppm 2.30-2.41 (m, 4H), 2.44-2.59 (m, 4H) 2.68 (s, 3H) 3.27 (s, 3H, overlapped with MeOH-d4) 3.87 (quin, J=8.30 Hz, 1H) 5.01-5.10 (m, 1H) 6.61 (d, J=3.51 Hz, 1H) 7.08 (d, J=3.71 Hz, 1H) 8.07 (s, 1H); LCMS (M/Z): 336 (M+H); retention time on Chiralpak IF-3 column: 8.59 min (broad peak).

By proceeding in similar fashion to previous examples, the following were prepared.

Example 28

Compound 28: 6-[methyl(7H-pyrrolo[2,3-d]pyrimidin-4-yl)amino]spiro[3.3]heptane-2-sulfonamide

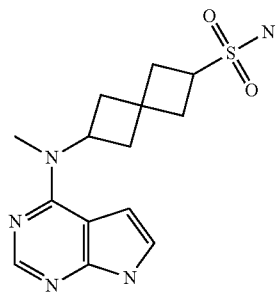 [SMILES: CN(c1ncnc2[nH]ccc12)C1CC2(C1)CC(S(N)(=O)=O)C2]

6-[methyl(7H-pyrrolo[2,3-d]pyrimidin-4-yl)amino]spiro[3.3]heptane-2-sulfonamide: $^1$H NMR (400 MHz, METHANOL-d4) δ ppm 8.07 (s, 1H), 7.08 (d, J=3.7 Hz, 1H), 6.62 (d, J=3.7 Hz, 1H), 5.13-5.00 (m, 1H), 3.83-3.72 (m, 1H), 3.28 (s, 3H, overlapped with MeOH-d4), 2.63-2.22 (m, 9H); LCMS (M/Z): 322 (M+H).

Example 29

Compound 29: N,N-dimethyl-6-[methyl(7H-pyrrolo[2,3-d]pyrimidin-4-yl)amino]spiro[3.3]heptane-2-sulfonamide

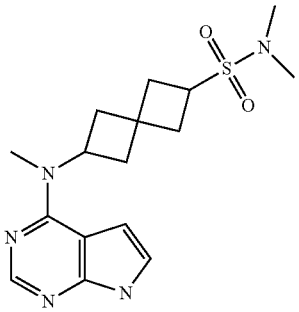

N,N-dimethyl-6-[methyl(7H-pyrrolo[2,3-d]pyrimidin-4-yl)amino]spiro[3.3]heptane-2-sulfonamide: $^1$H NMR (400 MHz, METHANOL-d4) δ ppm 8.07 (s, 1H), 7.08 (d, J=3.5 Hz, 1H), 6.62 (d, J=3.7 Hz, 1H), 5.13-5.01 (m, 1H), 3.93 (t, J=8.4 Hz, 1H), 3.28 (s, 3H), 2.82 (s, 6H), 2.65-2.46 (m, 4H), 2.41-2.26 (m, 4H); LCMS (M/Z): 350 (M+H).

Example 30

Compound 30: N-methyl-N-(2-pyrrolidin-1-ylsulfonylspiro[3.3]heptan-6-yl)-7H-pyrrolo[2,3-d]pyrimidin-4-amine

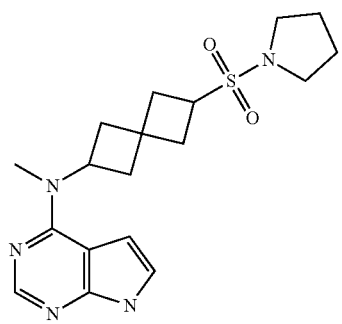 [SMILES: CN(c1ncnc2[nH]ccc12)C1CC2(C1)CC(S(=O)(=O)N1CCCC1)C2]

N-methyl-N-(2-pyrrolidin-1-ylsulfonylspiro[3.3]heptan-6-yl)-7H-pyrrolo[2,3-d]pyrimidin-4-amine: $^1$H NMR (400 MHz, METHANOL-d4) δ ppm 8.08 (br s, 1H), 7.08 (d, J=3.5 Hz, 1H), 6.62 (d, J=3.7 Hz, 1H), 5.16-4.95 (m, 1H), 3.96 (quin, J=8.4 Hz, 1H), 3.27 (s, 3H, overlapped with MeOH-d4), 2.69-2.21 (m, 8H), 1.97-1.83 (m, 4H); LCMS (M/Z): 376 (M+H).

Abbreviations

DCM=dichloromethane
DMA=dimethylacetamide
DMF=dimethylformamide
DMAP=4-dimethylaminopyridine
LAH=lithium aluminum hydride
NaH=sodium hydride
REDAl=sodium bis(2-methoxyethoxy)aluminum hydride
SEMCl=2-(Trimethylsilyl)ethoxymethyl chloride
TBAF=tetrabutyl ammonium fluoride
THF=tetrahydrofuran
TsCl=p-toluenesulfonyl chloride

Evaluation

The biological activity of compounds of the present invention was tested using the test methods described below.

The example compounds were screened for Jak1 activity at Thermo Fisher Scientific, using their Z'-Lyte™ protocol, as described below. Selectivity screening against other kinases can be performed following similar procedures.

Z'-LYTE Assay Conditions: The Test Compounds are screened in 1% DMSO (final) in the well. Three screening concentrations (10, 100, and 1000 nM) of test compounds were used.

Peptide/Kinase Mixtures: All Peptide/Kinase Mixtures are diluted to a 2× working concentration in the appropriate Kinase Buffer (For JAK1, the 2×JAK1/Tyr 06 mixture is prepared in 50 mM HEPES pH 6.5, 0.01% BRIJ-35, 10 mM MgCl2, 1 mM EGTA, 0.02% NaN3. The final 10 μL Kinase Reaction consists of 21.2-91.5 ng JAK1 and 2 μM Tyr 06 in 50 mM HEPES pH 7.0, 0.01% BRIJ-35, 10 mM MgCl2, 1 mM EGTA, 0.01% NaN3. After the 1 hour Kinase Reaction incubation, 5 μL of a 1:128 dilution of Development Reagent A is added).

ATP Solution: All ATP Solutions are diluted to a 4× working concentration in Kinase Buffer (50 mM HEPES pH 7.5, 0.01% BRIJ-35, 10 mM MgCl2, 1 mM EGTA).

ATP: Km apparent is previously determined using a Z'-LYTE assay.

10× Novel PKC Lipid Mix: 2 mg/ml Phosphatidyl Serine, 0.2 mg/ml DAG in 20 mM HEPES, pH 7.4, 0.3% CHAPS. For 5 mL 10× Novel PKC Lipid Mix:
1. Add 10 mgs Phosphatidyl Serine (Avanti Polar Lipids Part #8400032C or 840039C) and 1 mg DAG (Avanti Polar Lipids Part #800811C) to a glass tube.
2. Remove the chloroform from lipid mixture by evaporating to a clear, thin film under a stream of nitrogen. Continuous rotation of the tube, at an angle to ensure maximum surface area of the lipid solution, will promote the thinnest film.
3. Add 5 mLs resuspension buffer, 20 mM HEPES, 0.3% CHAPS, pH 7.4, to the dried lipid mix
4. Heat gently to 50-60° C. for 1-2 minutes and vortex in short intervals until the lipids are dissolved to a clear or slightly hazy solution. The lipids are typically in solution after 2-3 heat/vortex cycles.
5. Cool to room temperature, aliquot into single use volumes and store at −20° C.

Assay Protocol Bar-coded Corning, low volume NBS, black 384-well plate (Corning Cat. #4514)
1. 100 nL—100× Test Compound in 100% DMSO
2. 2.4 μL—Kinase buffer
3. 5 μL—2× Peptide/Kinase Mixture
4. 2.5 μL—4×ATP Solution
5. 30-second plate shake
6. 60-minute Kinase Reaction incubation at room temperature
7. 5 μL—Development Reagent Solution
8. 30-second plate shake
9. 60-minute Development Reaction incubation at room temperature
10. Read on fluorescence plate reader and analyze the data.

TABLE

Data Summary

| Compound | Compound Name | % Inhibition 10 nM | % Inhibition 100 nM | % Inhibition 1000 nm |
|---|---|---|---|---|
| 1 | N-methyl-6-[methyl(7H-pyrrolo[2,3-d]pyrimidin-4-yl)amino]spiro[3.3]heptane-2-sulfonamide | 71 | 92 | 96 |
| 2 | N-ethyl-6-[methyl(7H-pyrrolo[2,3-d]pyrimidin-4-yl)amino]spiro[3.3]heptane-2-sulfonamide | 52 | 90 | 98 |
| 3 | 6-[methyl(7H-pyrrolo[2,3-d]pyrimidin-4-yl)amino]-N-propyl-spiro[3.3]heptane-2-sulfonamide | 57 | 92 | 98 |
| 4 | N-isopropyl-6-[methyl(7H-pyrrolo[2,3-d]pyrimidin-4-yl)amino]spiro[3.3]heptane-2-sulfonamide | 23 | 75 | 95 |
| 5 | N-cyclopropyl-6-[methyl(7H-pyrrolo[2,3-d]pyrimidin-4-yl)amino]spiro[3.3]heptane-2-sulfonamide | 61 | 94 | 99 |

TABLE-continued

Data Summary

| Compound | Compound Name | % Inhibition 10 nM | % Inhibition 100 nM | % Inhibition 1000 nm |
|---|---|---|---|---|
| 6 | 6-[methyl(7H-pyrrolo[2,3-d]pyrimidin-4-yl)amino]-N-(2,2,2-trifluoroethyl)spiro[3.3]heptane-2-sulfonamide | 63 | 93 | 96 |
| 7 | N-isobutyl-6-[methyl(7H-pyrrolo[2,3-d]pyrimidin-4-yl)amino]spiro[3.3]heptane-2-sulfonamide | 42 | 88 | 97 |
| 8 | N-tert-butyl-6-[methyl(7H-pyrrolo[2,3-d]pyrimidin-4-yl)amino]spiro[3.3]heptane-2-sulfonamide | 37 | 82 | 94 |
| 9 | N-cyclobutyl-6-[methyl(7H-pyrrolo[2,3-d]pyrimidin-4-yl)amino]spiro[3.3]heptane-2-sulfonamide | 64 | 93 | 99 |
| 10 | N-cyclopentyl-6-[methyl(7H-pyrrolo[2,3-d]pyrimidin-4-yl)amino]spiro[3.3]heptane-2-sulfonamide | 52 | 84 | 97 |
| 11 | N-[2-[methyl(7H-pyrrolo[2,3-d]pyrimidin-4-yl)amino]spiro[3.3]heptan-6-yl]benzenesulfonamide | 11 | 81 | 95 |
| 12 | 2-chloro-N-[2-[methyl(7H-pyrrolo[2,3-d]pyrimidin-4-yl)amino]spiro[3.3]heptan-6-yl]benzenesulfonamide | 15 | 60 | 90 |
| 13 | 4-chloro-N-[2-[methyl(7H-pyrrolo[2,3-d]pyrimidin-4-yl)amino]spiro[3.3]heptan-6-yl]benzenesulfonamide | 27 | 77 | 95 |
| 14 | N-[2-[methyl(7H-pyrrolo[2,3-d]pyrimidin-4-yl)amino]spiro[3.3]heptan-6-yl]-4-(trifluoromethyl)benzenesulfonamide | 1 | 56 | 92 |
| 15 | N-[2-[methyl(7H-pyrrolo[2,3-d]pyrimidin-4-yl)amino]spiro[3.3]heptan-6-yl]methanesulfonamide | 31 | 78 | 95 |
| 16 | N-[2-[methyl(7H-pyrrolo[2,3-d]pyrimidin-4-yl)amino]spiro[3.3]heptan-6-yl]ethanesulfonamide | 28 | 76 | 96 |
| 17 | N-[2-[methyl(7H-pyrrolo[2,3-d]pyrimidin-4-yl)amino]spiro[3.3]heptan-6-yl]propane-1-sulfonamide | 38 | 83 | 95 |
| 18 | N-[2-[methyl(7H-pyrrolo[2,3-d]pyrimidin-4-yl)amino]spiro[3.3]heptan-6-yl]propane-2-sulfonamide | 23 | 71 | 94 |
| 19 | 2-methyl-N-[2-[methyl(7H-pyrrolo[2,3-d]pyrimidin-4-yl)amino]spiro[3.3]heptan-6-yl]propane-1-sulfonamide | 27 | 73 | 94 |
| 20 | N-[2-[methyl(7H-pyrrolo[2,3-d]pyrimidin-4-yl)amino]spiro[3.3]heptan-6-yl]cyclopentanesulfonamide | 33 | 82 | 97 |
| 21 | 3,3,3-trifluoro-N-[2-[methyl(7H-pyrrolo[2,3-d]pyrimidin-4-yl)amino]spiro[3.3]heptan-6-yl]propane-1-sulfonamide | 46 | 85 | 98 |
| 22 | N-((6-(methyl(7H-pyrrolo[2,3-d]pyrimidin-4-yl)amino)spiro[3.3]heptan-2-yl)methyl)methanesulfonamide | 76 | 96 | 96 |
| 23 | N-((6-(methyl(7H-pyrrolo[2,3-d]pyrimidin-4-yl)amino)spiro[3.3]heptan-2-yl)methyl)ethanesulfonamide | 66 | 94 | 97 |
| 24 | N-methyl-6-[methyl(9H-purin-6-yl)amino]spiro[3.3]heptane-2-sulfonamide | 4 | 21 | 72 |
| 25 | N-methyl-6-[methyl(1H-pyrazolo[3,4-d]pyrimidin-4-yl)amino]spiro[3.3]heptane-2-sulfonamide | 2 | 4 | 19 |
| 26 | (Enantiomer A)-N-methyl-6-[methyl(7H-pyrrolo[2,3-d]pyrimidin-4-yl)amino]spiro[3.3]heptane-2-sulfonamide | 77 | 96 | 98 |
| 27 | (Enantiomer B)-N-methyl-6-[methyl(7H-pyrrolo[2,3-d]pyrimidin-4-yl)amino]spiro[3.3]heptane-2-sulfonamide | 12 | 52 | 89 |
| 28 | 6-[methyl(7H-pyrrolo[2,3-d]pyrimidin-4-yl)amino]spiro[3.3]heptane-2-sulfonamide | 13 | 60 | 94 |
| 29 | N,N-dimethyl-6-[methyl(7H-pyrrolo[2,3-d]pyrimidin-4-yl)amino]spiro[3.3]heptane-2-sulfonamide | 55 | 92 | 98 |
| 30 | N-methyl-N-(2-pyrrolidin-1-ylsulfonylspiro[3.3]heptan-6-yl)-7H-pyrrolo[2,3-d]pyrimidin-4-amine | 43 | 89 | 99 |

Embodiments of the present disclosure include:

1. A compound of Formula I or a pharmaceutical or veterinary salt thereof

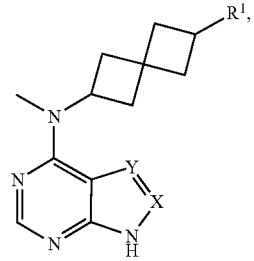

Formula I wherein

X is N, CH, or $CR^3$;

Y is N, CH, or $CR^3$;

$R^1$ is $(CH_2)_n SO_2 N(R^2)_2$, $(CH_2)_m NHSO_2 R^2$, $(CH_2)_n CON(R^2)_2$, or $(CH_2)_m NHCOR^2$ n is 0, 1, 2, 3, or 4;

m is 0, 1, 2, 3, or 4;

each $R^2$ individually is hydrogen, $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, unsubstituted or substituted cycloalkyl, unsubstituted or substituted aryl, or unsubstituted or substituted heteroaryl; or two $R^2$ may combine with the nitrogen to which they are attached to form an unsubstituted or substituted 5- to 7-membered ring, which may include one or more additional heteroatom selected from N, O, or S, and which may include one or more degrees of unsaturation;

and each $R^3$ individually is $C_{1-6}$ alkyl, $C_{1-6}$ haloalkyl, $C_{2-6}$ alkenyl, $C_{2-6}$ haloalkenyl, $C_{2-6}$ alkynyl, $C_{2-6}$ haloalkynyl, hydroxyl, $C_{1-6}$ alkoxy, $C_{1-6}$ haloalkyoxy, $C_{1-6}$ alkylsulfonyl, $C_1$-6 thioalkyl, mercapto, halogen, nitro, cyano, amino, $C_{1-6}$ alkylamino, unsubstituted or substituted cycloalkyl, unsubstituted or substituted aryl, or unsubstituted or substituted heteroaryl, when X is CR$^3$ and Y is CR$^3$, each CR$^3$ may combine, with the atoms to which they are attached, to form a fused 5 to 7 membered ring.

2. The compound of 1, wherein R$^1$ is (CH$_2$)$_n$SO$_2$NHR$^2$ or (CH$_2$)$_m$NHSO$_2$R$^2$.
3. The compound of 1 or 2, wherein R$^1$ is (CH$_2$)$_n$SO$_2$NHR$^2$
4. The compound of one of 1-3, wherein n is 0.
5. The compound of one of 1-3, wherein n is 1.
6. The compound of any one of 1-5, wherein R$^2$ is C$_{1-6}$ alkyl, unsubstituted or substituted cycloalkyl, C$_{1-6}$ haloalkyl, or unsubstituted or substituted aryl.
7. The compound of 6, wherein said cycloalkyl or aryl is substituted with one or more halogen, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, CN, NO$_2$, NH$_2$, N(C$_{1-6}$ alkyl)$_2$, OH, or OC$_{1-6}$ alkyl.
8. The compound of 1 or 2, wherein R$^1$ is (CH$_2$)$_m$NHSO$_2$R$^2$.
9. The compound of one of 1, 2, or 8, wherein m is 0.
10. The compound of one of 1, 2, or 9, wherein m is 1.
11. The compound of any one of 1, 2, or 8-10, wherein R$^2$ is C$_{1-6}$ alkyl, unsubstituted or substituted cycloalkyl, C$_{1-6}$ haloalkyl, or unsubstituted or substituted aryl.
12. The compound of 11, wherein said cycloalkyl or aryl is substituted with one or more halogen, C$_{1-6}$ alkyl, C$_{1-6}$ haloalkyl, C$_{2-6}$ alkenyl, C$_{2-6}$ haloalkenyl, C$_{2-6}$ alkynyl, C$_{2-6}$ haloalkynyl, CN, NO$_2$, NH$_2$, N(C$_{1-6}$ alkyl)$_2$, OH, or OC$_{1-6}$ alkyl.
13. The compound of any one of 1-12, wherein X is CH.
14. The compound of any one of 1-13, wherein Y is CH.
15. The compound of any one of 1-12, wherein one or more of X and Y is CR$^3$, where each R$^3$ is halogen, cyano, or C$_{1-6}$ alkyl.
16. A compound selected from:
N-methyl-6-[methyl(7H-pyrrolo[2,3-d]pyrimidin-4-yl)amino]spiro[3.3]heptane-2-sulfonamide;
N-ethyl-6-[methyl(7H-pyrrolo[2,3-d]pyrimidin-4-yl)amino]spiro[3.3]heptane-2-sulfonamide;
6-[methyl(7H-pyrrolo[2,3-d]pyrimidin-4-yl)amino]-N-propyl-spiro[3.3]heptane-2-sulfonamide;
N-isopropyl-6-[methyl(7H-pyrrolo[2,3-d]pyrimidin-4-yl)amino]spiro[3.3]heptane-2-sulfonamide;
N-cyclopropyl-6-[methyl(7H-pyrrolo[2,3-d]pyrimidin-4-yl)amino]spiro[3.3]heptane-2-sulfonamide;
6-[methyl(7H-pyrrolo[2,3-d]pyrimidin-4-yl)amino]-N-(2,2,2-trifluoroethyl)spiro[3.3]heptane-2-sulfonamide;
N-isobutyl-6-[methyl(7H-pyrrolo[2,3-d]pyrimidin-4-yl)amino]spiro[3.3]heptane-2-sulfonamide;
N-tert-butyl-6-[methyl(7H-pyrrolo[2,3-d]pyrimidin-4-yl)amino]spiro[3.3]heptane-2-sulfonamide;
N-cyclobutyl-6-[methyl(7H-pyrrolo[2,3-d]pyrimidin-4-yl)amino]spiro[3.3]heptane-2-sulfonamide;
N-cyclopentyl-6-[methyl(7H-pyrrolo[2,3-d]pyrimidin-4-yl)amino]spiro[3.3]heptane-2-sulfonamide;
N-[2-[methyl(7H-pyrrolo[2,3-d]pyrimidin-4-yl)amino]spiro[3.3]heptan-6-yl]benzenesulfonamide;
2-chloro-N-[2-[methyl(7H-pyrrolo[2,3-d]pyrimidin-4-yl)amino]spiro[3.3]heptan-6-yl]benzenesulfonamide;
4-chloro-N-[2-[methyl(7H-pyrrolo[2,3-d]pyrimidin-4-yl)amino]spiro[3.3]heptan-6-yl]benzenesulfonamide;
N-[2-[methyl(7H-pyrrolo[2,3-d]pyrimidin-4-yl)amino]spiro[3.3]heptan-6-yl]-4-(trifluoromethyl)benzenesulfonamide;
N-[2-[methyl(7H-pyrrolo[2,3-d]pyrimidin-4-yl)amino]spiro[3.3]heptan-6-yl]methanesulfonamide;
N-[2-[methyl(7H-pyrrolo[2,3-d]pyrimidin-4-yl)amino]spiro[3.3]heptan-6-yl]ethanesulfonamide;
N-[2-[methyl(7H-pyrrolo[2,3-d]pyrimidin-4-yl)amino]spiro[3.3]heptan-6-yl]propane-1-sulfonamide;
N-[2-[methyl(7H-pyrrolo[2,3-d]pyrimidin-4-yl)amino]spiro[3.3]heptan-6-yl]propane-2-sulfonamide;
2-methyl-N-[2-[methyl(7H-pyrrolo[2,3-d]pyrimidin-4-yl)amino]spiro[3.3]heptan-6-yl]propane-1-sulfonamide;
N-[2-[methyl(7H-pyrrolo[2,3-d]pyrimidin-4-yl)amino]spiro[3.3]heptan-6-yl]cyclopentanesulfonamide;
3,3,3-trifluoro-N-[2-[methyl(7H-pyrrolo[2,3-d]pyrimidin-4-yl)amino]spiro[3.3]heptan-6-yl]propane-1-sulfonamide;
N-((6-(methyl(7H-pyrrolo[2,3-d]pyrimidin-4-yl)amino)spiro[3.3]heptan-2-yl)methyl)methanesulfonamide;
N-((6-(methyl(7H-pyrrolo[2,3-d]pyrimidin-4-yl)amino)spiro[3.3]heptan-2-yl)methyl)ethanesulfonamide;
N-methyl-6-[methyl(9H-purin-6-yl)amino]spiro[3.3]heptane-2-sulfonamide;
(Enantiomer A)—N-methyl-6-[methyl(7H-pyrrolo[2,3-d]pyrimidin-4-yl)amino]spiro[3.3]heptane-2-sulfonamide;
(Enantiomer B)—N-methyl-6-[methyl(7H-pyrrolo[2,3-d]pyrimidin-4-yl)amino]spiro[3.3]heptane-2-sulfonamide;
6-[methyl(7H-pyrrolo[2,3-d]pyrimidin-4-yl)amino]spiro[3.3]heptane-2-sulfonamide;
N,N-dimethyl-6-[methyl(7H-pyrrolo[2,3-d]pyrimidin-4-yl)amino]spiro[3.3]heptane-2-sulfonamide; and
N-methyl-N-(2-pyrrolidin-1-ylsulfonylspiro[3.3]heptan-6-yl)-7H-pyrrolo[2,3-d]pyrimidin-4-amine,
or a veterinary or pharmaceutical salt thereof.
17. A composition comprising a compound of any one of 1-16, and a pharmaceutically or veterinary acceptable carrier.
18. A combination comprising a compound of any one of 1-16, and one or more other pharmaceutical or veterinary active substances.
19. A method for treating pruritus or atopic dermatitis comprising: administering to a subject in need thereof an effective amount of a compound of any one of 1-16.
20. The method of 19, wherein the subject is a mammal.
21. The method of 20, where in the mammal is selected from humans, cattle, sheep, goats, llamas, alpacas, pigs, horses, donkeys, dogs, cats, livestock mammals, domestic mammals, or companion mammals.
22. A compound of any one of 1-16 for use in medicine.
23. A compound of any one of 1-16 for the manufacture of a medicament for the treatment of pruritus or atopic dermatitis.
24. Use of a compound of any one of 1-16 for the treatment of pruritus or atopic dermatitis.

All publications, patents and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

The invention claimed is:

1. A compound selected from:

N-methyl-6-[methyl(7H-pyrrolo[2,3-d]pyrimidin-4-yl)amino]spiro[3.3]heptane-2-sulfonamide;

or a veterinary or pharmaceutical salt thereof.

2. A composition comprising a compound of claim 1 and a pharmaceutically or veterinary acceptable carrier.

3. A combination comprising a compound of claim 1 and one or more other pharmaceutical or veterinary active substances.

4. A method for treating pruritus or atopic dermatitis comprising:

administering to a subject in need thereof an effective amount of a compound of claim 1.

5. The method of claim 4, wherein the subject is a mammal.

6. The method of claim 5, where in the mammal is selected from humans, cattle, sheep, goats, llamas, alpacas, pigs, horses, donkeys, dogs, cats, livestock mammals, domestic mammals, or companion mammals.

* * * * *